US012230401B1

(12) United States Patent
Cui et al.

(10) Patent No.: US 12,230,401 B1
(45) Date of Patent: Feb. 18, 2025

(54) INTELLIGENT DECISION REASONING METHOD FOR TYPE-BASED DIAGNOSIS AND TREATMENT OF CARDIOVASCULAR DISEASE, DEVICE, AND PRODUCT

(71) Applicants: University of Science and Technology Beijing, Beijing (CN); Peking Union Medical College, Beijing (CN)

(72) Inventors: Hongzhen Cui, Beijing (CN); Meihua Piao, Beijing (CN); Yunfeng Peng, Beijing (CN); Shichao Wang, Beijing (CN); Longhao Zhang, Beijing (CN); Haoming Ma, Beijing (CN); Xiaoyue Zhu, Beijing (CN)

(73) Assignees: University of Science and Technology Beijing, Beijing (CN); Peking Union Medical College, Beijing (CN)

( * ) Notice: Subject to any disclaimer, the term of this patent is extended or adjusted under 35 U.S.C. 154(b) by 0 days.

(21) Appl. No.: 18/626,099

(22) Filed: Apr. 3, 2024

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *G16H 20/10* (2018.01); *G16H 50/70* (2018.01); *G16H 70/40* (2018.01)

(58) Field of Classification Search
CPC ........ G16H 50/20; G16H 10/60; G16H 20/10; G16H 50/70; G16H 70/40
(Continued)

(56) References Cited

U.S. PATENT DOCUMENTS

| 7,921,068 B2 * | 4/2011 | Guyon | ................ G06F 18/2411 706/45 |
| 2007/0092888 A1 * | 4/2007 | Diamond | ............. C12Q 1/6883 702/20 |

(Continued)

FOREIGN PATENT DOCUMENTS

| WO | WO-2019086867 A1 * | 5/2019 | ............. G06F 17/16 |
| WO | WO-2024200649 A1 * | 10/2024 | |

*Primary Examiner* — Robert A Sorey
*Assistant Examiner* — Kimberly A. Sass
(74) *Attorney, Agent, or Firm* — Nixon Peabody LLP

(57) ABSTRACT

The present disclosure provides an intelligent decision reasoning method for type-based diagnosis and treatment of a cardiovascular disease, a device, and a product, and relates to the medical field. The present disclosure adopts a risk factor mining model of a cardiovascular disease and a drug attribute association mining model of the cardiovascular disease to extract relevant information from cardiovascular data, achieving precise prediction of a fine-grained cardiovascular disease type and effectively promoting precision medicine. Based on a clinical diagnostic dataset and a clinical symptom diagnosis knowledge system of the cardiovascular disease, a type-based auxiliary diagnosis model of the cardiovascular disease is constructed, and intelligent decision reasoning is performed to obtain an association rule. This achieves efficient integration of type-based decision support of the cardiovascular disease and a medical convalescence knowledge base of the cardiovascular disease, and enhances quality of a cardiovascular medical convalescence association rule set.

17 Claims, 7 Drawing Sheets

(51) Int. Cl.
*G16H 20/10* (2018.01)
*G16H 50/70* (2018.01)
*G16H 70/40* (2018.01)

(58) Field of Classification Search
USPC .......................................................... 705/3
See application file for complete search history.

(56) References Cited

U.S. PATENT DOCUMENTS

2018/0342323 A1* 11/2018 Shankar ................. G16H 10/60
2022/0108085 A1*  4/2022 Pathak ................. G06V 30/413

* cited by examiner

US 12,230,401 B1

INTELLIGENT DECISION REASONING METHOD FOR TYPE-BASED DIAGNOSIS AND TREATMENT OF CARDIOVASCULAR DISEASE, DEVICE, AND PRODUCT

TECHNICAL FIELD

The present disclosure relates to the medical field, and in particular, to an intelligent decision reasoning method for type-based diagnosis and treatment of a cardiovascular disease, a device, and a product.

BACKGROUND

A cardiovascular disease is a common chronic disease of middle-aged and elderly people, and ranks first in mortality rates of major diseases among urban and rural residents. At present, a quantity of patients with the cardiovascular disease remains high, and the cardiovascular disease shows youth oriented tendency due to factors such as staying up late, smoking, alcoholism, and an unhealthy diet. This makes prevention and control of the cardiovascular disease become increasingly severe. Statistical analysis of past clinical data and sorting out a disease occurrence mechanism are main ideas of digital diagnosis and treatment. However, a "data island" and other problems occur due to diverse data organization forms and the like.

The artificial intelligence (AI) era makes it possible to energize diagnosis and treatment of the cardiovascular disease with data. However, the prior art often has limitations, which focuses on overall research on major cardiovascular disease types and pays less attention to prediction of fine-grained cardiovascular disease types, making it difficult to achieve precision medicine. Separation of diagnosis and treatment and a biased focus result in a lack of a focus on research of a type-based convalescence technology or insufficient evaluation of quality of an intelligent convalescence program, making it difficult to achieve a satisfactory convalescence effect. In addition, there is no specialized convalescence program recommendation technology tailored to an actual situation of a disease, and a drug recommendation alone is difficult to meet a comprehensive home-based wellness demand of a patient.

SUMMARY

In order to solve the above problems in the prior art, the present disclosure provides an intelligent decision reasoning method for type-based diagnosis and treatment of a cardiovascular disease, a device, and a product.

To achieve the above objective, the present disclosure provides following technical solutions.

An intelligent decision reasoning method for type-based diagnosis and treatment of a cardiovascular disease includes:
  constructing a risk factor mining model of a cardiovascular disease and a drug attribute association mining model of the cardiovascular disease;
  extracting common clinical symptoms, disease types, and medication attribute information of a plurality of types of cardiovascular diseases from cardiovascular data based on the risk factor mining model of the cardiovascular disease and the drug attribute association mining model of the cardiovascular disease, where the cardiovascular data includes: data of an electronic medical record of a cardiovascular patient, a cardiovascular medication guideline, clinical reception information, and expert consensus knowledge;
  constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases;
  constructing a type-based auxiliary diagnosis model of the cardiovascular disease based on the clinical diagnostic dataset and the clinical symptom diagnosis knowledge system of the cardiovascular disease, and using the type-based auxiliary diagnosis model of the cardiovascular disease for intelligent decision reasoning;
  constructing an association rule based on a reasoning result obtained through the intelligent decision reasoning;
  constructing a medical convalescence knowledge base of the cardiovascular disease based on convalescence data of the cardiovascular patient and the association rule; and
  generating a recommended patient wellness program based on a collaborative filtering algorithm and the medical convalescence knowledge base of the cardiovascular disease.

Optionally, the constructing a risk factor mining model of a cardiovascular disease and a drug attribute association mining model of the cardiovascular disease specifically includes:
  extracting consensus text data by using a document parsing technology, where the consensus text data includes text data of the electronic medical record of the cardiovascular patient and the cardiovascular medication guideline;
  adding a data annotation to the consensus text data to obtain annotated data, where the data annotation includes an entity type, a relationship type, and an attribute type; the attribute type includes a symptom, a cardiovascular disease type, a risk factor, a medical history, a biochemical indicator, a drug name, a medication type, a mode of administration, a medication frequency, a medication cycle, and a medication dosage;
  training a network model based on the annotated data, where the network model includes an input layer, a text information representation and embedding layer, a semantic information modeling layer, a label sequence correction and recognition layer, and an output layer; and
  separately using a trained network model as the risk factor mining model of the cardiovascular disease and the drug attribute association mining model of the cardiovascular disease.

Optionally, extracting the common clinical symptoms, the disease types, and the medication attribute information of the plurality of types of cardiovascular diseases from the consensus text data based on the risk factor mining model of the cardiovascular disease and the drug attribute association mining model of the cardiovascular disease specifically includes:
  performing named entity recognition for the consensus text data based on the risk factor mining model of the cardiovascular disease, where recognized content includes the symptom, the cardiovascular disease type, the risk factor, the medical history, and the biochemical indicator; and
  performing named entity recognition and association modeling of a cardiovascular related drug for the consensus text data based on the drug attribute association mining model of the cardiovascular disease to obtain recognized and mined content, where the recognized and mined content includes the drug name, the medication type, the mode of administration, the medication frequency, the medication cycle, a dosage form, and the medication dosage.

Optionally, the constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases specifically includes:

sorting out symptom data obtained by the risk factor mining model of the cardiovascular disease, and forming clinical diagnostic symptom indicators and expert clinical diagnosis knowledge systems of the plurality of types of cardiovascular diseases based on expert guidance, an expert experience knowledge system, and an expert consensus; and constructing the clinical diagnostic dataset of the cardiovascular disease based on the clinical diagnostic symptom indicators and types of the cardiovascular diseases; setting values of the clinical diagnostic symptom indicators of the cardiovascular diseases to 1, 0, or more clinically meaningful cardiovascular disease numbers or letters based on a symptom representation; and setting different values for different types of cardiovascular diseases to complete the construction of the clinical diagnostic dataset and the clinical symptom diagnosis knowledge system of the cardiovascular disease.

Optionally, a process of obtaining the reasoning result through the intelligent decision reasoning includes:

determining conditional mutual information between symptom nodes, and ranking the conditional mutual information between the symptom nodes in descending order to obtain a set of the conditional mutual information between the symptom nodes;

based on the set of the conditional mutual information between the symptom nodes, designing a maximum weighted spanning tree according to a principle of selecting an edge without generating a loop;

adding a disease type node to the maximum weighted spanning tree to obtain a Bayesian network structure;

determining a conditional probability table of a Bayesian network based on the Bayesian network structure and the clinical diagnostic dataset of the cardiovascular disease;

forming a Tree-Augmented Naive Bayes (TAN) model for type-based decision-making of the cardiovascular disease based on the Bayesian network structure and the conditional probability table of the Bayesian network; and determining a probability of each cardiovascular disease type based on the type-based decision-supported TAN model of the cardiovascular disease, and selecting a type with a maximum probability as a disease type.

Optionally, the constructing a medical convalescence knowledge base of the cardiovascular disease based on convalescence data of the cardiovascular patient and the association rule specifically includes:

constructing a medical convalescence transaction set of the cardiovascular disease based on the cardiovascular data, where the medical convalescence transaction set of the cardiovascular disease includes medical convalescence transaction subsets of the plurality of types of cardiovascular diseases; a medical convalescence transaction subset of each type of cardiovascular disease includes a corresponding patient portrait and a medical convalescence record set of the cardiovascular disease; the patient portrait includes basic information and a disease type of a patient; the basic information of the patient includes an age, a height, and a weight; the medical convalescence record set of the cardiovascular disease includes a convalescence item; and the convalescence item includes drug, diet, and exercise data;

when l=1, generating a frequent itemset 1 through screening based on a support degree of a single convalescence itemset, where the l represents a type of the medical convalescence transaction subset of the cardiovascular disease in the medical convalescence transaction set of the cardiovascular disease;

when l≥2, generating a candidate itemset 1 based on a frequent itemset (l−1);

searching for a non-frequent itemset (l−1) in the candidate itemset 1, and if the non-frequent itemset exists, performing pre-pruning to remove the non-frequent itemset;

generating a frequent itemset l through screening based on the candidate itemset/and the support degree, performing the step of generating the candidate itemset/based on the frequent itemset (l−1) when l≥2 until there is no itemset meeting a minimum support degree, and forming a set based on the frequent itemset 1;

traversing an element in the set and determining a proper subset of the element, generating the association rule through permutation and combination, performing filtering based on a confidence coefficient and an enhancement degree to form a medical convalescence association rule set that is of the cardiovascular disease and corresponds to each type of patient portrait; and constructing the medical convalescence knowledge base of the cardiovascular disease based on the medical convalescence association rule set that is of the cardiovascular disease and corresponds to each type of patient portrait.

Optionally, the generating a recommended patient wellness program based on a collaborative filtering algorithm and the medical convalescence knowledge base of the cardiovascular disease specifically includes:

marking basic information of a to-be-recommended patient, where the basic information includes an age, a height, a weight, a medical history, a disease, and a treatment process;

inputting a clinical symptom of the to-be-recommended patient into the type-based decision-supported TAN model of the cardiovascular disease to output a cardiovascular disease typing result;

integrating the basic information of the to-be-recommended patient and the cardiovascular disease typing result to form a portrait of the to-be-recommended patient:

determining a distance between the portrait of the to-be-recommended patient and a patient portrait in the medical convalescence knowledge base of the cardiovascular disease; and selecting, from the medical convalescence knowledge base of the cardiovascular disease, a medical convalescence association rule set that is of the cardiovascular disease and corresponds to a patient portrait with a smallest distance from the portrait of the to-be-recommended patient as the recommended patient wellness program.

A computer device includes a memory, a processor, and a computer program stored in the memory and executable on the processor, where the processor executes the computer program to perform the steps of the intelligent decision reasoning method for type-based diagnosis and treatment of a cardiovascular disease described above.

A computer program product includes a computer program, where the computer program is executed by a processor to perform the steps of the intelligent decision reasoning method for type-based diagnosis and treatment of a cardiovascular disease described above.

According to specific embodiments provided in the present disclosure, the present disclosure has following technical effects:

The present disclosure adopts a risk factor mining model of a cardiovascular disease and a drug attribute association mining model of the cardiovascular disease to extract common clinical symptoms, disease types, and medication attribute information of a plurality of types of cardiovascular diseases from cardiovascular data, achieving precise prediction of a fine-grained cardiovascular disease type and effectively promoting precision medicine. Based on a clinical diagnostic dataset and a clinical symptom diagnosis knowledge system of the cardiovascular disease, a type-based auxiliary diagnosis model of the cardiovascular disease is constructed for intelligent decision reasoning to construct an association rule. This achieves efficient integration of type-based decision support of the cardiovascular disease and a medical convalescence knowledge base of the cardiovascular disease, and enhances quality of a cardiovascular medical convalescence association rule set. Based on convalescence data of a cardiovascular patient and the association rule, the medical convalescence knowledge base of the cardiovascular disease is constructed to generate a recommended patient wellness program, which can provide a target group with customized convalescence knowledge such as a drug, a diet, and exercise, effectively meeting a home-based wellness demand of the target group.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION OF THE EMBODIMENTS

The technical solutions of the embodiments of the present disclosure are clearly and completely described below with reference to the accompanying drawings in the embodiments of the present disclosure. Apparently, the described embodiments are merely a part rather than all of the embodiments of the present disclosure. All other embodiments obtained by those skilled in the art based on the embodiments of the present disclosure without creative efforts shall fall within the protection scope of the present disclosure.

An objective of the present disclosure is to provide an intelligent decision reasoning method for type-based diagnosis and treatment of a cardiovascular disease, a device, and a product to achieve integrated precise digital diagnosis and treatment.

In order to make the above objective, features, and advantages of the present disclosure clearer and more comprehensible, the present disclosure will be further described in detail below in combination with the accompanying drawings and particular implementations.

Embodiment 1

Figure 1:
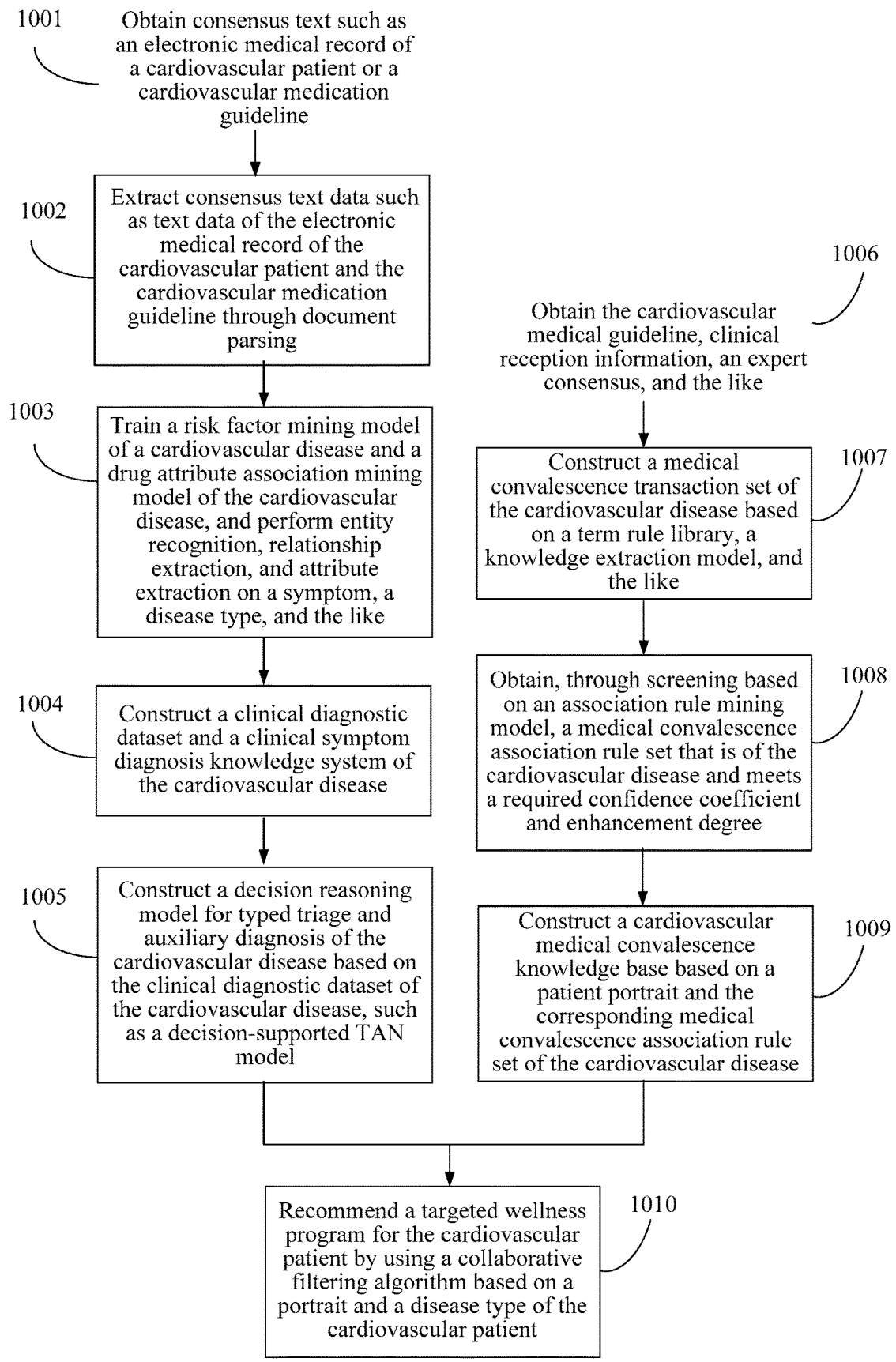
FIG. 1 shows an overall implementation process according to Embodiment 1 of the present disclosure.

As shown in FIG. 1, an intelligent decision reasoning method for type-based diagnosis and treatment of a cardiovascular disease in this embodiment includes following steps:

Step 1001: Obtain consensus text data such as an electronic medical record of a cardiovascular patient or a cardiovascular medication guideline.

Step 1002: Extract the consensus text data such as the electronic medical record of the cardiovascular patient or the cardiovascular medication guideline through document parsing. The consensus text data such as text data of the electronic medical record of the cardiovascular patient or the cardiovascular medication guideline can be extracted through a document parsing technology including but not limited to optical character recognition (OCR). The text data of the electronic medical record of the cardiovascular patient includes but is not limited to a clinical symptom, a diagnostic disease type, and the like.

Step 1003: Train a risk factor mining model of a cardiovascular disease and a drug attribute association mining model of the cardiovascular disease, and perform entity recognition, relationship extraction, and attribute extraction on a symptom, a disease type, and the like. In other words, the risk factor mining model of the cardiovascular disease and the drug attribute association mining model of the cardiovascular disease are constructed based on data of the electronic medical record of the cardiovascular patient, and common clinical symptoms, disease types, and medication attribute information of a plurality of types of cardiovascular diseases are extracted. The common clinical symptom of the cardiovascular disease includes but is not limited to a shock, dizziness, a chest pain, difficult breathing, and the like. The risk factor mining model of the cardiovascular disease outputs text content, including a cause of the cardiovascular disease, such as obesity, hypertension, hyperlipidemia, a high salt diet, smoking, alcoholism, or other pathogenic factors (cardiovascular disease).

The disease type includes a first-type disease and a subordinate second-type disease. The first-type disease includes but is not limited to cardiomyopathy, arrhythmia, the hypertension, a coronary heart disease, and the like. Taking the cardiomyopathy as an example, the subordinate second-type disease includes but is not limited to dilated cardiomyopathy, primary cardiomyopathy, secondary cardiomyopathy, specific cardiomyopathy, and the like.

The symptom includes but is not limited to the shock, the dizziness, the chest pain, the difficult breathing, and the like.

A risk factor includes but is not limited to the smoking, the alcoholism, a poor diet, heredity, the obesity, mood, dyslipidemia, diabetes, the hypertension, and the like.

A medical history includes but is not limited to a current medical history, a past medical history, and a family medical history.

A biochemical indicator includes but is not limited to cholesterol, triglycerides, blood sugar, myocardial enzymes, troponin, myoglobin, and other related biochemical indicators.

A drug name includes but is not limited to a related drug that is used for treatment of the cardiovascular disease and covered by the cardiovascular medication guideline, for example, an opioid drug.

A relationship between medication attributes such as a medication type, a mode of administration, a medication frequency, a medication cycle, and a medication dosage is correspondingly mined, recognized, and extracted based on the above drug name, a clinical record, medical record information, a medication guideline, and the like.

In an actual application, a process of the step 1003 may include following steps:

Step 1003-1: Add a data annotation to the consensus text data such as the text data of the electronic medical record of the cardiovascular patient or the cardiovascular medication guideline by using a method including but not limited to BIO, BMES, and BIOSE. The data annotation includes an entity type, a relationship type, and an attribute type. The attribute type includes but is not limited to the symptom, a cardiovascular disease type, the risk factor, the medical history, the biochemical indicator, the drug name, the medication type, the mode of administration, the medication frequency, the medication cycle, the medication dosage, and the like.

Step 1003-2: Train the risk factor mining model of the cardiovascular disease and the drug attribute association mining model of the cardiovascular disease based on annotated data. The risk factor mining model of the cardiovascular disease and the drug attribute association mining model of the cardiovascular disease include but are not limited to an input layer, a text information representation and embedding layer, a semantic information modeling layer, a label sequence correction and recognition layer, an output layer, and other structures.

For the electronic medical record, the medication guideline, a medication consensus, and the like, the drug attribute association mining model of the cardiovascular disease outputs a drug and a corresponding medication attribute. For example, the cardiovascular medication guideline includes a following sentence: "Dosage, impact, and adverse reaction of lovastatin: Initially take 20 mg at dinner time daily, and gradually increase to 80 mg daily, which is taken in one or two doses." The drug attribute association mining model of the cardiovascular disease can output following information:

(1) Lovastatin-medication dosage-20 mg.
(2) Lovastatin-medication dosage-80 mg.
(3) Lovastatin-medication frequency-once.
(4) Lovastatin-medication frequency-twice.
(5) Lovastatin-mode of administration-taken orally.

The medication dosage, the medication frequency, the medication cycle, the adverse reaction, and the mode of administration belong to drug attribute associations. In a natural language processing and knowledge graph, the drug name is referred to as an entity, and the drug attribute association is referred to as a "relationship".

Figure 2:
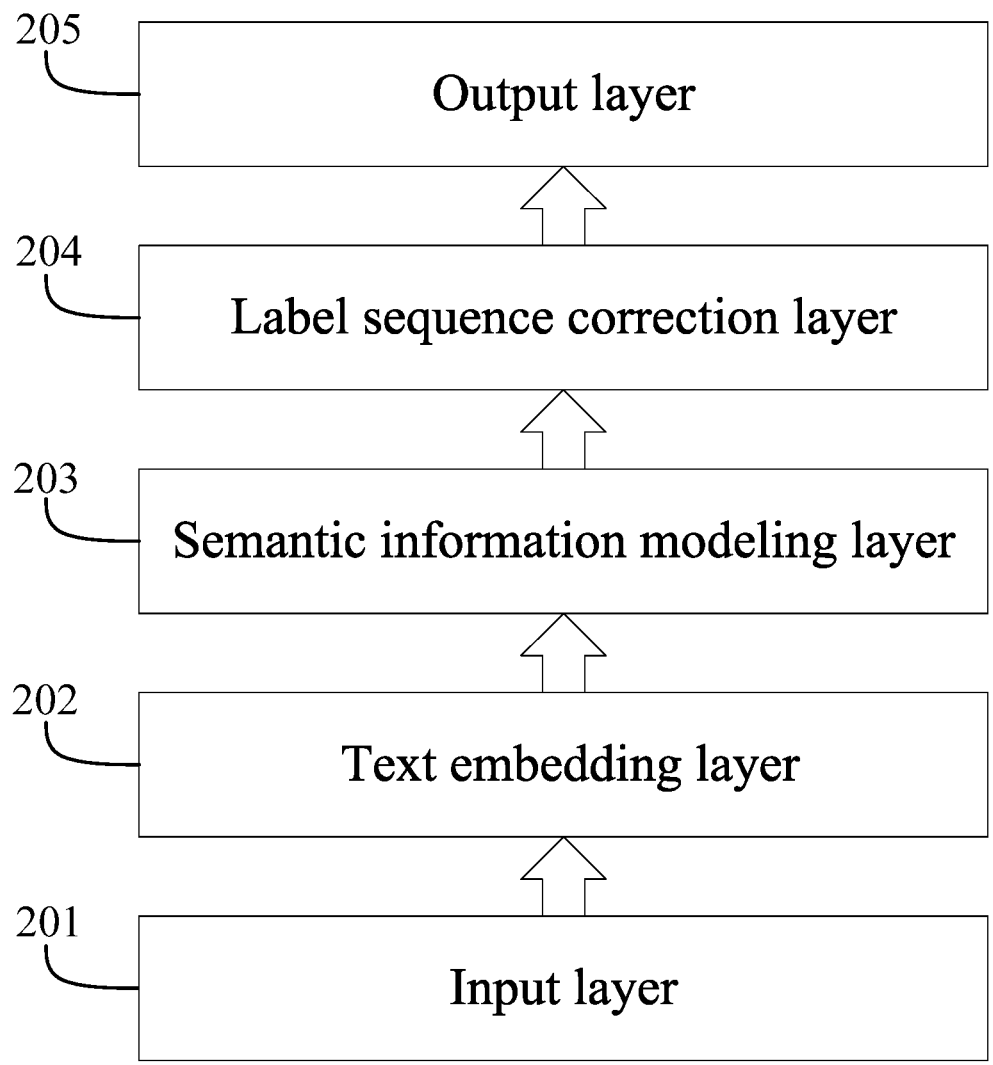
FIG. 2 is a structural diagram of a risk factor mining model of a cardiovascular disease according to Embodiment 1 of the present disclosure.

For example, the risk factor mining model of the cardiovascular disease and the drug attribute association mining model of the cardiovascular disease are of a five-layer structure, as shown in FIG. 2. The five-layer structure of each of the risk factor mining model of the cardiovascular disease and the drug attribute association mining model of the cardiovascular disease includes the input layer 201, the text information representation and embedding layer 202, the semantic information modeling layer 203, the label sequence correction and recognition layer 204, and the output layer 205.

The input layer 201 is configured to receive a training corpus for the risk factor mining model of the cardiovascular disease and the drug attribute association mining model of the cardiovascular disease, for example "large vessel disease", "cardiovascular disease", or "reducing a start dosage of sustained-release metoprolol (CR/XL formula) to 12.5 mg for a severe cardiac failure".

The text embedding layer 202 includes but is not limited to various network model structures that can achieve text vectorization, such as BERT and XLNet. The text embedding layer 202 can integrate information including but is not limited to text semantic information, positional information, and the like, to achieve corpus vectorization. For example, an input of the BERT includes a word vector, a statement segment vector, and a position vector. The word vector is obtained by using a model including but not limited to One-hot, Word2vec, or the like. The sentence segment vector is used to distinguish different clauses and capture a semantic relation between the clauses. The position vector is used to capture position information of a Chinese character, a word, a character, a special character, and the like.

The semantic information modeling layer 203 includes but is not limited to various network model structures that can capture contextual semantic information, such as a BILSTM and a BiGRU. The semantic information modeling layer 203 performs semantic modeling based on forward and reverse semantic information extraction structures. For example, the BILSTM includes a forward LSTM layer that captures contextual information $\overrightarrow{h}_t$ and a reverse LSTM layer that captures reverse information $\overleftarrow{h}_t$. An output $h_t$ of the BiLSTM is as follows:

$$h_t=[\overrightarrow{h}_t, \overleftarrow{h}_t]$$

The label sequence correction layer 204 includes but is not limited to various network model structures that ensure legitimacy of a label sequence by adding a constraint, such as a CRF. The label sequence correction layer 204 performs corrective recognition on a predicted label sequence output by the semantic information modeling layer, and obtains an optimal solution based on a probability relationship between adjacent labels. Taking the CRF as an example, the semantic information modeling layer generates a following prediction result (cardiovascular disease as an example for segmentation):

| Car- | -dio- | -vascular | di- | -sease |
|------|-------|-----------|-----|--------|
| B-n  | I-ns  | I-n       | I-n | I-n    |

The CRF corrects the prediction result based on a constraint and generates a following output:

| Car B-n | dio I-n | vascular I-n | di I-n | sease I-n |
|---------|---------|--------------|--------|-----------|

The output layer 205 is configured to generate a label sequence prediction result corresponding to a text corpus of the input layer.

Step 1003-3: Perform named entity recognition for the consensus text data such as the text data of the electronic medical record of the cardiovascular patient and the cardiovascular medication guideline based on the risk factor mining model of the cardiovascular disease, where recognized content includes the symptom, the cardiovascular disease type, the risk factor, the medical history, the biochemical indicator, and other information.

Step 1003-4: Perform named entity recognition and association modeling of a cardiovascular related drug for the consensus text data such as the text data of the electronic medical record of the cardiovascular patient and the cardiovascular medication guideline based on the drug attribute association mining model of the cardiovascular disease, where recognized and mined content includes the but is not limited the drug name, the medication type, the mode of administration, the medication frequency, the medication cycle, a dosage form, the medication dosage, and the like.

Step 1004: Construct a clinical diagnostic dataset and a clinical symptom diagnosis knowledge system of the cardiovascular disease. Specifically, the clinical diagnostic dataset and the clinical symptom diagnosis knowledge system of the cardiovascular disease are constructed through data preprocessing based on the common clinical symptom and a diagnosis result of the cardiovascular disease.

In an actual application, a process of the step 1004 may include following steps:

Step 1004-1: Sort out symptom data extracted by the risk factor mining model of the cardiovascular disease, and form clinical diagnostic symptom indicators and expert clinical diagnosis knowledge systems of the plurality of types of cardiovascular diseases based on expert guidance, an expert experience knowledge system, and an expert consensus.

Step 1004-2: Construct the clinical diagnostic dataset of the cardiovascular disease based on the clinical diagnostic symptom indicators and types of the cardiovascular diseases, as shown in Table 1; set values of the clinical diagnostic symptom indicators of the cardiovascular diseases to 1, 0, or more clinically meaningful cardiovascular disease numbers or letters based on a symptom representation; and set different values for different cardiovascular disease types, for example, set the clinical diagnostic symptom indicator to 0 for the cardiomyopathy and 1 for the arrhythmia.

TABLE 1

Structure table of the clinical diagnostic dataset of the cardiovascular disease

| SN | Symptom indicator 1 | Symptom indicator 2 | ... | Symptom indicator n | Disease type |
|----|---------------------|---------------------|-----|---------------------|--------------|
| 1  | 1                   | 0                   | ... | 1                   | 1 (hypertension) |
| 2  | 0                   | 1                   | ... | 1                   | 2 (coronary heart disease) |
| .  | .                   | .                   | .   | .                   | . |
| .  | .                   | .                   | .   | .                   | . |
| .  | .                   | .                   | .   | .                   | . |
| m  | 0                   | 0                   | ... | 1                   | a (cardiomyopathy) |

Step 1005: Construct a decision reasoning model for type-based triage and auxiliary diagnosis of the cardiovascular disease based on the clinical diagnostic dataset of the cardiovascular disease, such as a decision-supported TAN model. Specifically, a type-based auxiliary diagnosis model of the cardiovascular disease is constructed based on the clinical diagnostic dataset and the knowledge system of the cardiovascular disease, in other words, an intelligent decision reasoning model is achieved. The decision reasoning model includes but is not limited to improved decision reasoning models based on machine learning, statistics, deep learning, and other models. Based on the clinical dataset, a disease type (a cardiovascular disease type) of a patient can be predicted. Based on the disease type mentioned above, a treatment recommendation (medication, weight loss, surgery, or the like) is provided based on the disease type and the medication guideline. The treatment recommendation herein corresponds to the type-based auxiliary diagnosis model of the cardiovascular disease.

Construction of a type-based decision-supported TAN model of the cardiovascular disease is taken as an example to assist in decision-making of the disease type.

In an actual application, a process of the step 1005 may include following steps:

Step 1005-1: Calculate conditional mutual information $I_{s_i,s_j}$ between symptom nodes, and rank the conditional mutual information between the symptom nodes in descending order to obtain a set S of the conditional mutual information between the symptom nodes.

Step 1005-2: Based on the S, design a maximum weighted spanning tree according to a principle of selecting an edge without generating a loop. A disease type node is added to the maximum weighted spanning tree to obtain a Bayesian network structure.

Step 1005-3: Calculate a conditional probability table of a Bayesian network based on the Bayesian network structure and the clinical diagnostic dataset of the cardiovascular disease. The type-based decision-supported TAN model of the cardiovascular disease is composed of the Bayesian network structure and the conditional probability table of the Bayesian network.

Step 1005-4: Calculate a probability of each cardiovascular disease type based on the type-based decision-supported TAN model of the cardiovascular disease, and select a type with a maximum probability as a disease type It. In an actual application, more than one disease type may be obtained for a patient based on a series of symptoms. For example, difficult breathing may be a symptom of diseases such as a cardiac failure, the coronary heart disease, and myocardial infarction. Therefore, based on the TAN model, probabilities of the above three diseases are given. For example, the probability of the cardiac failure is 60%, and both the probability of the coronary heart disease and the probability of the myocardial infarction is 20%. So, a final disease type obtained through type-based decision support is the cardiac failure.

The TAN model provides a probability of the disease type of the patient, that is, a probability of the patient suffering from a disease X is Y.

Taking six types of cardiovascular symptoms as an example, a process of constructing the type-based decision-supported TAN model of the cardiovascular disease is specifically as follows:

1) Calculate the conditional mutual information $I_{s_i,s_j}$ between the symptom nodes, and rank the conditional mutual information between the symptom nodes in descending order to obtain the set S of the conditional mutual information between the symptom nodes. Taking the symptom nodes $s_i, s_j$ i≠j as an example, the conditional mutual information $I_{s_i,s_j}$ between them is calculated according to a following method:

$$I_{s_i,s_j} = \sum_{s_i,s_j,C} P(s_i; s_j; C) \log_2 \frac{P(s_i; s_j|C)}{P(s_i|C)P(s_j|C)}.$$

In the above formula, C represents the cardiovascular disease type, $P(s_i; s_j; C)$ represents an overall proportion of a sample with the cardiovascular disease type C and a symptom $s_i, s_j$, $P(s_i; s_j|C)$ represents a proportion of the sample with the known disease type C and the symptom $s_i$, $s_j$ in this type of group, $P(s_i|C)$ represents a proportion of a sample with the known disease type C and a symptom $s_i$ in this type of group, $P(s_j|C)$ represents a proportion of a sample with the known disease type C and a symptom $s_j$ in the this type of group.

The set S of the conditional mutual information between the symptom nodes is as follows:

$$S=[I_1,I_2,\ldots,I_t]=[I_{s_1,s_2},I_{s_1,s_2},\ldots],I_t \leq I_{t-1}.$$

In the above formula, t represents a quantity of combination types of different symptom nodes $s_i, s_j$.

Figure 3:
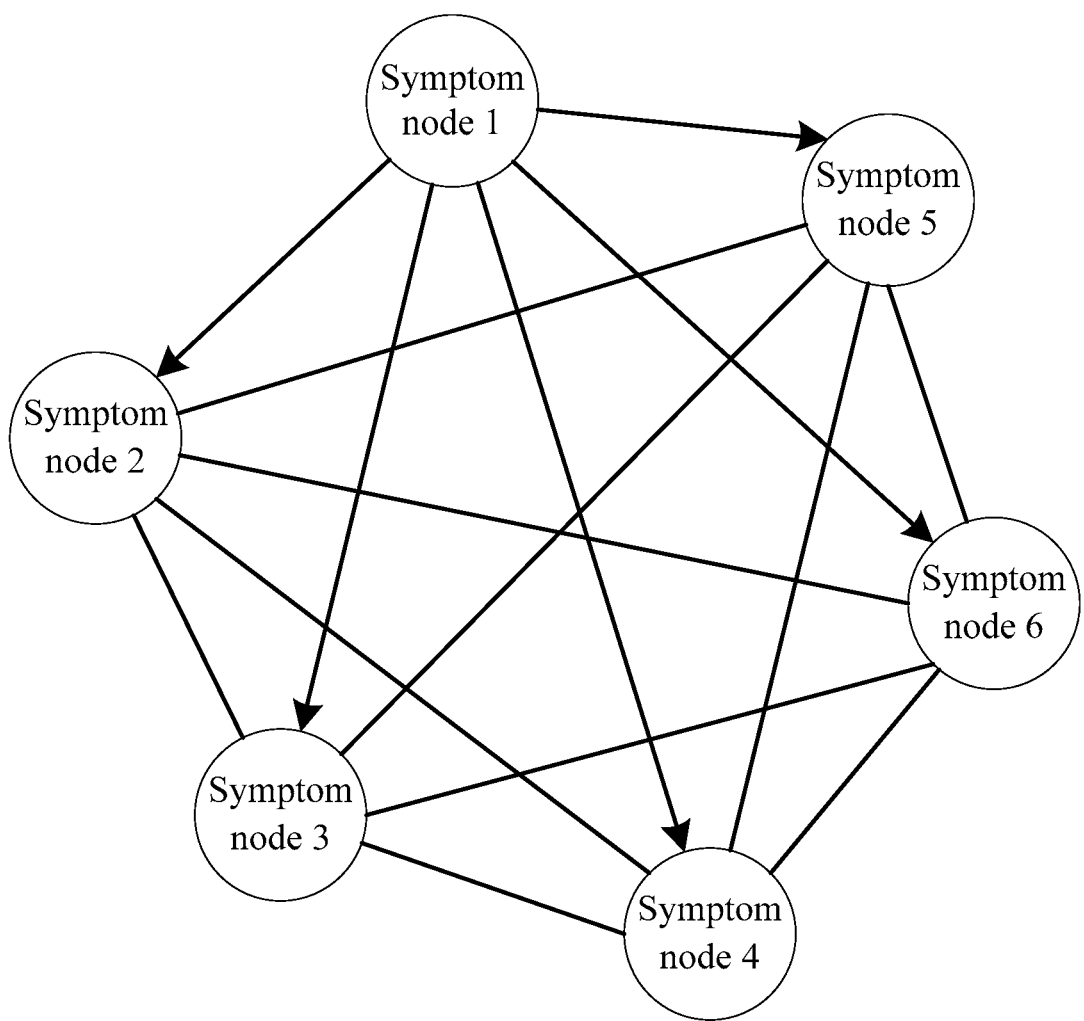
FIG. 3 is a structural diagram of a maximum weighted spanning tree according to Embodiment 1 of the present disclosure.

2) Based on the set S of the conditional mutual information between the symptom nodes, design the maximum weighted spanning tree according to the principle of selecting the edge without generating the loop. The maximum weighted spanning tree is shown in FIG. 3. Conditional mutual information $I_{s_1,s_2}$, $I_{s_1,s_3}$, $I_{s_1,s_4}$, $I_{s_1,s_5}$, $I_{s_1,s_6}$ takes the top 5 places in the set S of the conditional mutual information between the symptom nodes, namely:

$$S=[I_{s_1,s_2},I_{s_1,s_3},I_{s_1,s_4},I_{s_1,s_5},I_{s_1,s_6},\ldots].$$

Figure 4:
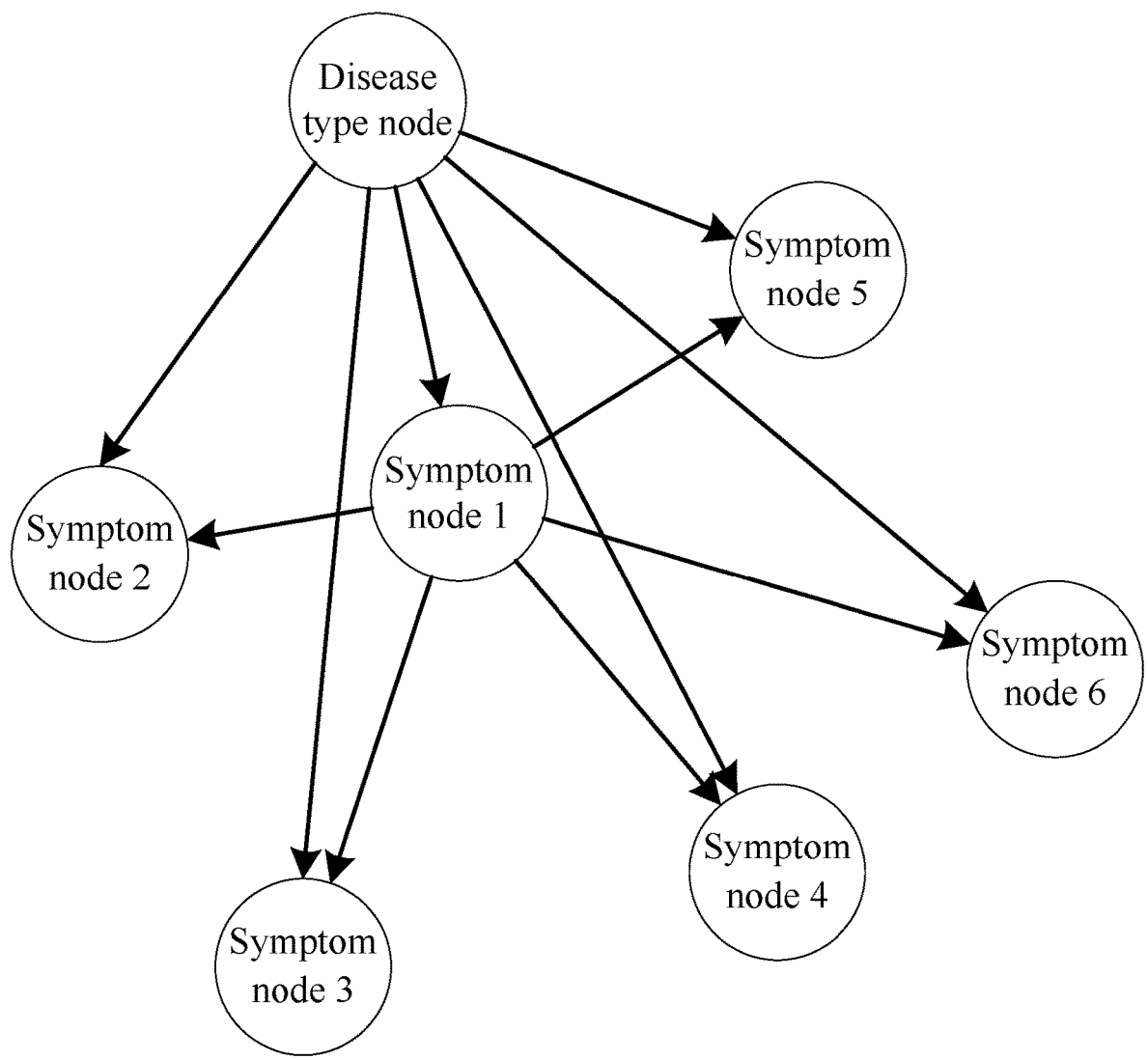
FIG. 4 is a structural diagram of a Bayesian network according to Embodiment 1 of the present disclosure.

As shown in FIG. 4, the disease type node is added to the maximum weighted spanning tree to obtain the Bayesian network structure.

3) Calculate the conditional probability table of the Bayesian network based on the Bayesian network structure and the clinical diagnostic dataset of the cardiovascular disease. A structure of the conditional probability table of the Bayesian network is shown in Table 2 to Table 4, including a probability table for each disease type (Table 2), a conditional probability table for a symptom node 1 (Table 3) and the disease type, and a conditional probability table for the symptom node j, j≠1, the symptom node 1, and the cardiovascular disease type (Table 4).

In FIG. 3, a value $P(C=It_i)$ of the probability table for each disease type is calculated according to a following method:

$$P(C = It_i) = \frac{N_{It_i}}{N}, i \in [1, b].$$

In the above formula, $NIT_i$ represents a quantity of samples with a disease type $It_i$, N represents a total quantity of samples in the dataset, and b represents a quantity of cardiovascular disease types.

TABLE 2

Disease probability table of the Bayesian network

| Disease type | Probability $^p$ |
| --- | --- |
| Hypertension | |
| . | Probability |
| . | |
| Cardiomyopathy | |

TABLE 3

Symptom node probability table of the Bayesian network

| Symptom node 1 | Hypertension | . . . | Cardiomyopathy |
| --- | --- | --- | --- |
| 0 | | Probability | |
| 1 | | | |

TABLE 4

Symptom node probability table of the Bayesian network

| | Hypertension | | . . . | Cardiomyopathy | |
| --- | --- | --- | --- | --- | --- |
| Symptom node $^i$ | Symptom node i = 0 | Symptom node i = 1 | | Symptom node i = 0 | Symptom node i = 1 |
| 0 | Probability | Probability | | Probability | Probability |
| 1 | Probability | Probability | | Probability | Probability |

A value $P(s_1|It_i)$ of the conditional probability table for the symptom node 1 and the disease type is calculated according to a following method:

$$P(s_1|It_i) = \frac{N_{s_1,It_i}}{N_{It_i}}, i \in [1, b].$$

In the above formula, $N_{s_1,IT_i}$ represents a quantity of samples with the disease type $It_i$ and the symptom $s_1$.

A value $P(s_j|It_i, s_1)$ of the conditional probability table for the symptom node j, the symptom node 1, and the cardiovascular disease type is calculated according to a following method:

$$P(s_j|It_i, s_1) = \frac{N_{s_j,s_1,It_i}}{N_{s_1,It_i}}, i \in [1, b], j \neq 1.$$

In the above formula, $N_{s_j,s_1,It_i}$ represents a quantity of samples with the disease type I and the symptom $s_1$, $s_j$.

The type-based decision-supported TAN model of the cardiovascular disease is composed of the Bayesian network structure and the conditional probability table of the Bayesian network.

4) Calculate the probability of each cardiovascular disease type based on the type-based decision-supported TAN model of the cardiovascular disease, and select the type with the maximum probability as the disease type It $$C(It_i) = P(C = It_i) * P(s_1|It_i) \prod_{j=2}^{6} P(s_j|s_1, It_i), i \in [1, b], j \neq 1.$$

$It_i \text{argmax}[C(It_i)]$.

In an actual application, an implementation pseudocode for constructing the type-based decision-supported TAN model of the cardiovascular disease is as follows:

cular disease, which includes medical convalescence transaction subsets $\{Ts_i | i \in [1, n]\}$ of the plurality of types of cardiovascular diseases, where n represents a quantity of portrait types of the cardiovascular patient.

A medical convalescence transaction subset $Ts_i$ (represented by 502 in FIG. 5) of an $i^{th}$ type of cardiovascular disease consists of an $i^{th}$ patient portrait $U_i$ (represented by 503) and a medical convalescence record set $\{R_{i,j} | j \in [1, m]\}$ (represented by 504) of the $i^{th}$ type of cardiovascular disease, where m represents a quantity of medical convalescence records of the $i^{th}$ type of cardiovascular disease.

$Ts_i = [U_i, \{R_{i,j}, j \in [1,m]\}], i \in [1,n]$

The $i^{th}$ type of patient portrait $U_i$, $i \in [1, n]$ consists of basic patient information $Ub_i$ and a disease type $It_i$. The basic

---

Algorithm 1 Algorithm for constructing a TAN model for type-based decision-making of a cardiovascular disease Input: Cardiovascular clinical diagnostic dataset D
Output: Bayesian network structure and Bayesian conditional probability table
1:  Denote a total quantity of clinical symptom types of the cardiovascular disease as n, a total quantity of samples
    in the cardiovascular clinical diagnostic dataset as N, and a total quantity of cardiovascular disease types as m
2:  Denote a set of conditional mutual information between symptom nodes as S = [ ]
3:  for i = 1 → n − 1 do
4:    for j = 1 + 1 → n do
5:      Calculate conditional mutual information $I_{si,sj}$ between a symptom node i and a symptom node j
        according to a formula 1
6:      S.add(($s_i$, $s_j$, $I_{si,sj}$))
7:    end for
8:  end for
9:  Sort conditional mutual information in the S in descending order to obtain a set S'
10: Take the first n values, and draw a maximum weighted spanning tree based on symptom node numbers in
    the first n values
11: Add a disease type node to the maximum weighted spanning tree to obtain the Bayesian network structure
12: for j = 1 → n + 1 do        ▷ Traverse the Bayesian network structure to form the Bayesian
    conditional probability table
13:   if the node j is a disease type node then
14:     for k = 1 → m do
15:       Calculate a probability $P_k$ of a disease type k according to a formula 2
16:     end for
17:   else if the node j is a symptom node and a parent node does not include the symptom node then
18:     for x = 1 → $V_j$ do        ▷ $V_j$ represents a quantity of value types of the symptom node
19:       for k = 1 → m do
20:         Calculate a probability $P_{x/k}$ of a symptom x under the disease type k according to a formula 3
21:       end for
22:     end for
23:   else if the node j is a symptom node and the parent node includes the symptom node then
24:     for y = 1 → $W_j$ do        ▷ $W_j$ represents a quantity of value types of the symptom node
25:       for k = 1 → m do
26:         for x = 1 → $V_p$ do        ▷ $V_p$ represents a quantity of values of a parent symptom node
27:           Calculate a probability $P_{y/x;k}$ of a symptom y under the disease type k and the
           symptom x according to a formula 4
28:         end for
29:       end for
30:     end for
31:   end if
32:   Fill the probability $P_k$ or $P_{x/k}$ or $P_{y/x;k}$ in a Bayesian conditional probability table in a form shown in Table 3
33: end for
34: Integrate the Bayesian network structure and the Bayesian conditional probability table to form the TAN model
    for type-based decision-making of the cardiovascular disease

---

Step 1006: Obtain the cardiovascular medical guideline, clinical reception information, the expert consensus, and the like.

Figure 5:
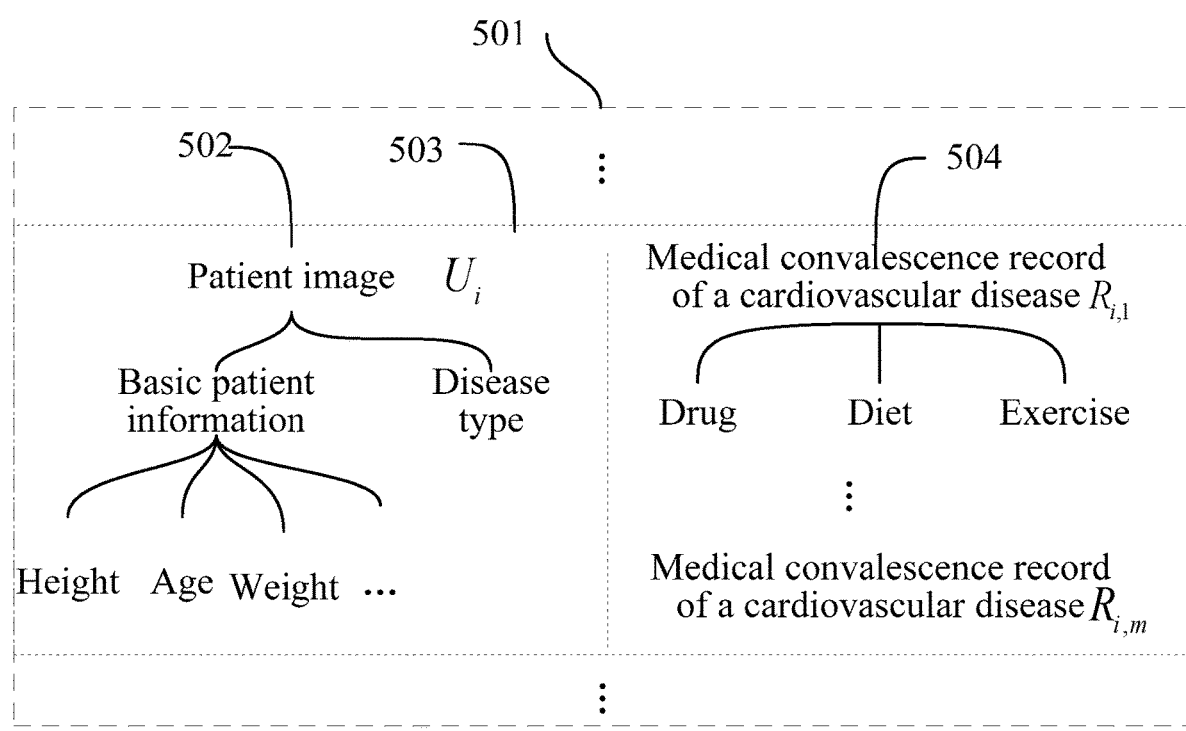
FIG. 5 is a schematic constitutional diagram of a medical convalescence transaction set of a cardiovascular disease according to Embodiment 1 of the present disclosure.

Step 1007: Construct a medical convalescence transaction set of the cardiovascular disease based on a term rule library, a knowledge extraction model, and the like. For example, based on the cardiovascular medical guideline, the clinical reception information, the expert consensus, and the like, a medical convalescence transaction set T of the cardiovascular disease is constructed by using a method including but not limited to the term rule library, the knowledge extraction model, and the like. As shown in FIG. 5, 501 represents the medical convalescence transaction set T of the cardiovaspatient information $Ub_i$ includes but is not limited to an age $u_i^{age}$, a height $u_i^{height}$, a weight $u_i^{weight}$, and other information. The $i^{th}$ type of patient portrait and the basic patient information are expressed as follows:

$U_i = [Ub_i, It_i], i \in [1,n]$ $Ub_i = [u_i^{age}, u_i^{height}, u_i^{weight}, \ldots]$.

An element $R_{i,j}$ in the medical convalescence record set of the $i^{th}$ type of med diet cardiovascular disease consists of convalescence items such as a drug $r_{i,j}^{med}$ a diet $r_{i,j}^{diet}$, and exercise $r_{i,j}^{spo}$.

$R_{i,j} = [r_{i,j}^{med}, r_{i,j}^{diet}, r_{i,j}^{spo}]$

In the above formula, $r_{i,j}^{med}$, $r_{i,j}^{diet}$, $r_{i,j}^{spo}$ each include 0 to any drug, diet, exercise item. For example, a value of $r_{i,j}^{med}$ may be Ø, {aspirin}, and {lacidipine, clopidogrel}.

Further, the term rule library includes an extraction rule for the medical convalescence transaction set of the cardiovascular disease, which is described based on a regular expression. For example, an age extraction rule is "\d+years of age", and a weight extraction rule is "\d+[.]?(\d)*kg".

The knowledge extraction model mines proper nouns of the cardiovascular disease type, the drug, the diet, the exercise, and other types by using models including but not limited to a pre-training model, a text embedding model, a semantic extraction model, and the like.

Step 1008: Obtain, through screening based on an association rule mining model, a medical convalescence association rule set that is of the cardiovascular disease and meets a required confidence coefficient and enhancement degree.

Step 1009: Construct a medical convalescence knowledge base of the cardiovascular disease based on the patient portrait and the corresponding medical convalescence association rule set of the cardiovascular disease.

An implementation process of the steps 1006 to 1009 is essentially to construct the medical convalescence knowledge base of the cardiovascular disease, structurally store convalescence knowledge, and form a cardiovascular treatment and wellness knowledge base system based on convalescence data of the cardiovascular patient and the association rule mining model. The association rule (model) herein is to establish a following knowledge structure for a symptom, a disease, a medication, a complication, an adverse reaction, and the like that exist in a treatment process of a patient, and form a knowledge base.

(1) Lovastatin-treatment-cardiac failure.
(2) Lovastatin-medication dosage-80 mg.
(3) Cardiac failure-symptom-difficult breathing.
(4) Cardiac failure-complication-acute pulmonary edema . . . .

Figure 6:
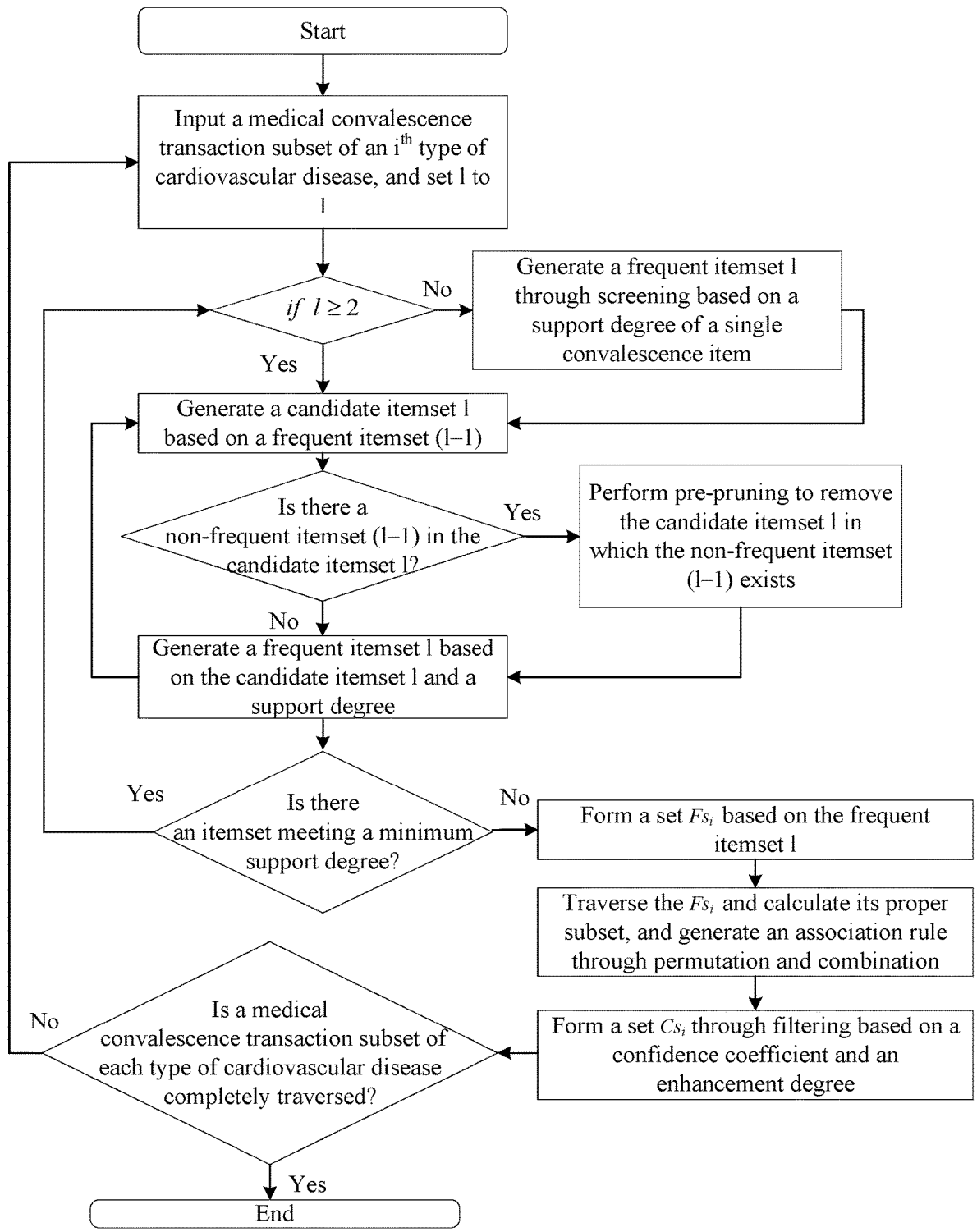
FIG. 6 is a flowchart of an association rule mining algorithm according to Embodiment 1 of the present disclosure.

As shown in FIG. 6, taking the medical convalescence transaction subset $Ts_i$ of the $i^{th}$ type of cardiovascular disease as an example, a specific process of mining the association rule is as follows:

S1: When l=1, generate a frequent itemset 1 through screening based on a support degree of a single convalescence itemset. The 1 represents a type of a medical convalescence transaction subset of the cardiovascular disease in the medical convalescence transaction set of the cardiovascular disease.

$$Sup(X_j^1) = \frac{N_{X_j^1}}{N_{Ts_i}}, i \in [1, n], j \in [1, d_i^1].$$

In the above formula, $Sup(X^*_j)$ represents a frequent itemset * generated through screening based on a support degree of a convalescence itemset in a medical convalescence transaction subset of a $j^{th}$ type of cardiovascular disease, and $N_{X^j}$ represents a quantity of times that a single convalescence itemset appears in the medical convalescence transaction subset $Ts_i$ of the $i^{th}$ type of cardiovascular disease, the single convalescence itemset may be, for example, {aspirin}, {celery}, or {jogging}, $N_{Ts_i}$ represents a total quantity of records in the medical convalescence transaction subset $Ts_i$ the $i^{th}$ type of cardiovascular disease, and represents a quantity of types of single convalescence itemsets in the medical convalescence transaction subset $Ts_i$ of the $i^{th}$ type of cardiovascular disease.

A minimum support degree is denoted as $z$, and a candidate itemset 1 that meets the minimum support degree is selected as the frequent itemset 1, namely:

$$Sup(X_j^1) \geq z, j \in [1, d_i^1]$$

The minimum support degree is artificially determined.

S2: When l≥2, generate a candidate itemset l based on a frequent itemset (l-1).

For example, a candidate itemset 2 is generated based on the frequent itemset 1. Assuming that the frequent itemset 1 in the S1 is $\{X_1^1, X_3^1, X_4^1, X_5^1, X_7^1\}$, the candidate itemset 2 generated through permutation and combination is as follows:

| $\{X_1^1, X_3^1\}$ | $\{X_1^1, X_4^1\}$ | $\{X_1^1, X_5^1\}$ | $\{X_1^1, X_7^1\}$ | $\{X_3^1, X_4^1\}$ |
| $\{X_3^1, X_5^1\}$ | $\{X_3^1, X_7^1\}$ | $\{X_4^1, X_5^1\}$ | $\{X_4^1, X_7^1\}$ | $\{X_5^1, X_7^1\}$ |

A support degree of each itemset in the candidate itemset 2 is calculated as follows:

$$Sup(X_j^2) = \frac{N_{X_j^2}}{N_{Ts_i}}, i \in [1, n], j \in [1, d_i^2],$$

$N_{X_j^2}$ = quantity of candidate itemset 2 of type $j$.

In the above formula, $d_i^2$ represents a type quantity of the candidate itemset 2 in the medical convalescence transaction subset $Ts_i$ of the $i^{th}$ type of cardiovascular disease, which is set to 10 herein. A candidate itemset 2 that meets the minimum support degree is selected as a frequent itemset 2, in other words, $$Sup(X_j^2) \geq z, j \in [1, d_i^2]$$

S3: Search for a non-frequent itemset (l-1) in the candidate itemset l, and if the non-frequent itemset exists, perform pre-pruning to remove the non-frequent itemset.

A candidate itemset 3 is taken as an example. It is assumed that the selected frequent itemset 2 in the S4-3 is as follows:

$$\{X_1^1, X_3^1\}\{X_1^1, X_4^1\}\{X_3^1, X_4^1\}\{X_3^1, X_5^1\}\{X_4^1, X_5^1\}\{X_5^1, X_7^1\}$$

The candidate itemset 3 generated based on the frequent itemset 2 is as follows:

| $\{X_1^1, X_3^1, X_4^1\}$ | $\{X_1^1, X_3^1, X_5^1\}$ | $\{X_1^1, X_4^1, X_5^1\}$ | $\{X_3^1, X_4^1, X_5^1\}$ | $\{X_3^1, X_5^1, X_7^1\}$ | $\{X_4^1, X_5^1, X_7^1\}$ |

Whether a non-frequent itemset 2 exists in the candidate itemset 3. If the non-frequent itemset 2 exists, the candidate itemset 3 is removed. Because $\{X_1^1, X_5^1\}$, $\{X_3^1, X_7^1\}$, $\{X_4^1, X_7^1\}$ is the non-frequent itemset 2, a candidate itemset 3 retained after the pre-pruning is as follows:

$$\boxed{\{X_1^1, X_3^1, X_4^1\}} \quad \boxed{\{X_3^1, X_4^1, X_5^1\}}$$

S4: Generate a frequent itemset 1 through screening based on the candidate itemset 1 and the support degree.

Taking the candidate itemset 3 as an example, a support degree of each itemset is calculated according to a following method:

$$Sup(X_j^3) = \frac{N_{x_j^3}}{N_{Ts_i}}, i \in [1, n], j \in [1, d_i^3],$$

$N_{x_j^3}$ = quantity of candidate itemset 3 of type $j$.

A frequent itemset 3 is obtained through screening based on the minimum support degree, in other words, $$Sup(X_j^3) \geq z, j \in [1, d_i^3]$$

S5. Repeat the steps S4-3 to S4-5 until there is no itemset meeting the minimum support degree.

S6: Form a set $Fs_i$ based on the frequent itemset 1, traverse an element of the set $Fs_i$, calculate a proper subset of the element, generate the association rule through the permutation and combination, and perform filtering based on the confidence coefficient and the enhancement degree to form a set.

It is assumed that the finally generated frequent itemset 1 is the frequent itemset 3:

$$\{X_1^1, X_3^1, X_4^1\}$$

Therefore, a following formula is obtained:

$$Fs_i = [\{X_1^1, X_3^1, X_4^1\}]$$

In actual calculation, there may be more than one element in the set $Fs_i$, and only an example is provided herein.

The element of the set $Fs_i$ is traversed, the proper subset of the element is calculated, the association rule is generated through the permutation and combination, and the filtering is performed based on the confidence coefficient and the enhancement degree to form the set $Cs_i$. The set $Fs_i$ is formed based on the frequent itemset 3, and the proper subset of the element of the set $Fs_i$ is as follows:

$$\{X_1^1\}\{X_3^1\}\{X_4^1\}\{X_1^1, X_4^1\}\{X_3^1, X_4^1\}$$

The association rule is generated by performing the permutation and combination on the above proper subset:

$$\{X_1^1\} \to \{X_3^1\}\{X_1^1\} \to \{X_4^1\} \quad \{X_3^1\} \to \{X_1^1\}\{X_3^1\} \to \{X_4^1\} \quad \{X_4^1\} \to \{X_1^1\}\{X_4^1\} \to \{X_3^1\}$$

$$\{X_1^1\} \to \{X_3^1, X_4^1\} \quad \{X_3^1\} \to \{X_1^1, X_4^1\} \quad \{X_4^1\} \to \{X_1^1, X_3^1\}$$

$$\{X_3^1, X_4^1\} \to \{X_1^1\} \quad \{X_1^1, X_4^1\} \to \{X_3^1\} \quad \{X_1^1, X_3^1\} \to \{X_4^1\}$$

The above association rule is traversed, and its confidence coefficient and enhancement degree are calculated. For example, the confidence coefficient of $\{X_3^1\} \to \{X_1^1, X_4^1\}$ is calculated according to a following method:

$$Con(\{X_3^1\} \to \{X_1^1, X_4^1\}) = \frac{Sup(\{X_1^1, X_3^1, X_4^1\})}{Sup(\{X_3^1\})}.$$

The enhancement degree of the association rule is calculated according to a following method:

$$Lift(\{X_3^1\} \to \{X_1^1, X_4^1\}) = \frac{Con(\{X_3^1\} \to \{X_1^1, X_4^1\})}{Sup(\{X_1^1, X_4^1\})}.$$

It is assumed that the confidence coefficient Con $(\{X_3^1\} \to \{X_1^1, X_4^1\})$ meets a required minimum confidence coefficient $\gamma$ specified artificially, in other words, Con $(\{X_3^1\} \to \{X_1^1, X_4^1\}) \geq \gamma$.

In addition, the enhancement degree is Lift$(\{X_3^1\} \to \{X_1^1, X_4^1\}) > 1$.

Therefore, this association rule is retained. Confidence coefficients and enhancement degrees of other association rules are calculated in a similar manner and can be screened based on the required minimum confidence coefficient and a required minimum enhancement degree.

S7: Repeat the steps S1 to S6 to generate a medical convalescence association rule set $Cs_i$, $i \in [1, n]$ that is of the cardiovascular disease and corresponds to each type of patient portrait $U_i$.

S8: As shown in Table 5, organize data in a form of the patient portrait $U_i$ and the medical convalescence association rule set $Cs_i$ based on the medical convalescence knowledge base of the cardiovascular disease to form the medical convalescence knowledge base of the cardiovascular disease. The organizing data is to form a set using a patient portrait and a corresponding convalescence rule. Then, a (new) patient portrait is used for collaborative filtering to retrieve a corresponding convalescence rule, and the retrieved convalescence rule is recommended to a (new) patient.

TABLE 5

Structure table of the medical convalescence knowledge base of the cardiovascular disease

| Patient portrait | | | | Medical convalescence |
|---|---|---|---|---|
| Basic patient information | | | | record of the cardiovascular disease |
| Age | Height/ cm | Weight/ kg | ... Disease type | |
| 50 | 100 | 65 | ... Hypertension | (Valsartan, jujube, jogging) (Vasodilator, celery) |

TABLE 5-continued

Structure table of the medical convalescence knowledge base of the cardiovascular disease

| Patient portrait | | | | Medical convalescence record of the cardiovascular disease |
|---|---|---|---|---|
| Basic patient information | | | | |
| Age | Height/ cm | Weight/ kg | ... Disease type | |

.
.
.
.
.

Based on the above description, an implementation pseudocode for constructing the medical convalescence knowledge base of the cardiovascular disease is as follows:

---

Algorithm 2 Algorithm for constructing a cardiovascular medical convalescence knowledge base Input: Cardiovascular medical guideline, clinical reception information, expert consensuses, and other corpus data
Output: Cardiovascular medical convalescence knowledge base Kb
1: Construct a medical convalescence transaction set T of a cardiovascular disease by extracting the cardiovascular medical guideline, the clinical reception information, the expert consensuses, and the other corpus data based on a terminology rule library, a knowledge extraction model, and the like
2: Denote a medical convalescence transaction set of an $i^{th}$ type of cardiovascular disease as $Ts_i$, which is a basic constitutional unit of the T
3: Denote an $i^{th}$ type of patient portrait as $U_i$ and a medical convalescence record of the cardiovascular disease as $R_{i,j}$, which are basic constitutional elements of the $Ts_i$
4: Denote a total quantity of patient portrait types in the T as n, a minimum support degree as $\zeta$, and a minimum confidence coefficient as $\psi$
5: for i = 1 → n do        ▷ Cyclically traverse patient portraits in the medical convalescence transaction set of the cardiovascular disease
6:    Denote a candidate itemset 1 of the medical convalescence transaction set of the $i^{th}$ type of cardiovascular disease as $X_j^1$
7:    l = 1        ▷ Quantity of saved itemsets
8:    if i = 1 then        ▷ Candidate itemset 1
9:        for j = 1 → $d_i^1$ do        ▷ $d_i^1$ represents a type quantity of the candidate itemset 1
10:            $Sup(X_j^1) = N_{X_j 1}/N_{Ts}$,        ▷ $N_{X_j 1}$ represents a quantity of a $j^{th}$ type of candidate itemsets 1, and $N_{T\,si}$ represents a total quantity of records
11:            if $Sup(X_j^1)$ $\zeta$ then
12:                $S_1.add(X_j^1)$        ▷ $S_1$ represents a set constituted by a frequent itemset 1
13:            end if
14:        end for
15:    end if
16:    l = l + 1
17:    if l > 1 then        ▷ A plurality of candidate itemsets
18:        while True do
19:            Traverse $S_{l-1}$, and form a set $S_l$ of a candidate itemset l through permutation and combination
20:            for α = 1 → $|S_l|$ do        ▷ Execute a pre-pruning operation
21:                if $X_α^1$ does not include a non-frequent itemset then        ▷ $X_α^l$ represents the candidate itemset 1, l > 1
22:                    $S_l'.add(X_α^l)$
23:                end if
24:            end for
25:            $S_l$ = [ ]
26:            for b = 1 → $|S_l'|$ do        ▷ Determine whether the candidate itemset l meets the minimum support degree
27:                $Sup(Xn_b^l) = N_{Xn_b l}/N_{Ts}$        ▷ $Xn_b^l$ represents a candidate itemset l after the pre-pruning
28:                if then $Sup(Xn_b^l) \geq \zeta$ $S_l.add(Xn_b^l)$
29:                end if
30:            end for
31:            if $|S_l|$ = θ then
32:                break
33:            end if
34:            l = l + 1
35:        end while
36:    end if
37:    Cyclically traverse the $S_l$, and take elements of a proper subset of the $S_l$ to form a new set Sn
38:    for i = 1 → |Sn| do
39:    Calculate a confidence coefficient $Con_i$ of $Rule_i$ according to a formula 5        ▷ $Rule_i$ represents an $i^{th}$ association rule
40:    Calculate an enhancement degree $Lift_i$ of the $Rule_i$ according to a formula 6
41:        if $Con_i \geq \psi$ and $Lift_i > 1$ then
42:            $Cs_i.add(Rule_i)$
43:        end if
44:    end for

| Algorithm 2 Algorithm for constructing a cardiovascular medical convalescence knowledge base |
| --- |
| 45: end for |
| 46: Form the cardiovascular medical convalescence knowledge base based on each $Cs_i$ and the cardiovascular patient portrait $U_i$ |

Step 1010: Recommend a targeted wellness program for the cardiovascular patient by using a collaborative filtering algorithm based on the portrait and the disease type of the cardiovascular patient. In other words, the wellness program is recommended to the patient based on the collaborative filtering algorithm and the medical convalescence knowledge base of the cardiovascular disease.

Figure 7:
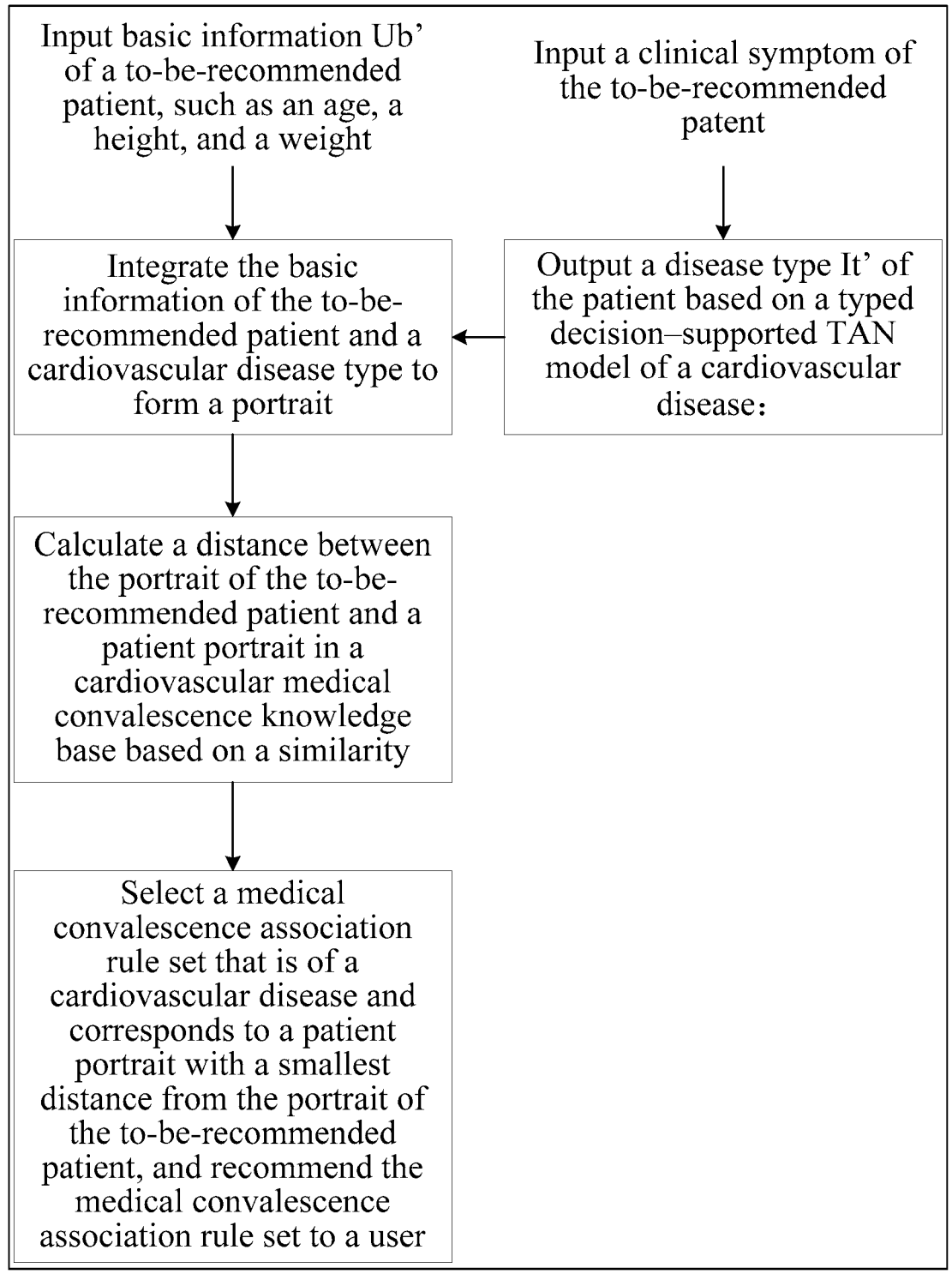
FIG. 7 is a flowchart of a patient caring program recommendation method according to Embodiment 1 of the present disclosure.

In an actual application, as shown in FIG. 7, an implementation process of the step 1010 may include following steps:

Step 1010-1: Denote basic information such as an age, a height, a weight, a medical history, a disease, a treatment process of a to-be-recommended patient as Ub', such that:

$$Ub'=[t_1, t_2, \ldots, t_o]$$

In the above formula, o represents a quantity of types of basic information, and $t_i$, $i \in [1, o]$ represents content of the basic information, such as the height.

Step 1010-2: Input a clinical symptom of the to-be-recommended patient based on the type-based decision-supported TAN model or more decision reasoning models to output a cardiovascular disease typing result It' of the to-be-recommended patient, and integrate the basic information of the to-be-recommended patient and the cardiovascular disease typing result to form a portrait U' of the to-be-recommended patient:

$$U'=[Ub', It']=[t_1, t_2, \ldots, t_o, It'].$$

Step 1010-3: Calculate a distance $d_{U'U_i}$ between the portrait U' of the to-be-recommended patient and the patient portrait $U_i$ in the medical convalescence knowledge base of the cardiovascular disease by using a method including but not limited to a cosine similarity, a Jaccard similarity coefficient, a Euclidean distance, a Manhattan distance, and the like according to a following formula:

$d_{U'U_i}$=distance(U', $U_i$), where n represents a quantity of patient portrait types in the medical convalescence knowledge base of the cardiovascular disease.

Taking the cosine similarity as an example, a calculation method is as follows:

$$d_{U'U_i} = simlarity(U', U_i) = \frac{t_1 t_{i,1} + t_2 t_{i,2} + \ldots + t_o t_{i,o} + It' It_i}{\sqrt{t_1^2 + \ldots + t_o^2 + It'^2} + \sqrt{t_{i,1}^2 + \ldots + t_{i,o}^2 + It_i^2}},$$

$$i \in [1, n].$$

In the above formula, $t_{i,j}$, $j \in [1, o]$ represents a $j^{th}$ type of basic patient information in the $i^{th}$ type of patient portrait.

Step 1010-4: Recommend a medical convalescence association rule set $Cs_m$ that is of the cardiovascular disease and corresponds to a minimum distance to the patient, where the medical convalescence association rule set $Cs_m$ that is of the cardiovascular disease and corresponds to the minimum distance is expressed as follows:

$$Cs_m s \cdot t \cdot \min(d_{U'U_i}).$$

In an actual application, an implementation pseudocode for recommending a caring program to the patient based on the collaborative filtering algorithm and the medical convalescence knowledge base of the cardiovascular disease is as follows:

| Algorithm 3 Algorithm for recommending a patient caring program |
| --- |
| Input: Basic information Ub' of a patient, clinical symptom It' of the patient, and cardiovascular medical convalescence knowledge base Kb<br>Output: Symptomatic caring program Mp of the patient<br>1: For the basic information Ub' = [$t_1$, $t_2$, ... ,$t_o$] of the patient based on a height, a weight, an age, and the like<br>2: Denote a clinical symptom set of the patient as $I_s$=[$s_1$, $s_2$ ··· ,$s_n$], and a typed decision-supported TAN model of a cardiovascular disease as $f_1$<br>3: Input the $I_s$ into the $f_1$ to obtain a cardiovascular disease type It' = $f_1$(Is) of the patient<br>4: Form a patient portrait U' = [Ub' , It'] based on the basic information Ub' of the patient and the cardiovascular disease type It'<br>5: Denote a minimum distance of the patient portrait as $d_{min}$=0, and a total quantity of patient portrait types as k<br>6:   for i = 1 → k do<br>7:     d = ($t_1$ * $t_{i,1}$ +...+ $t_o$ * $t_{i,o}$ + It' * $It_i$)/[sqrt($t_1^2$ +...+ $t_o^2$ + $It^2$) + sqrt($t_{i,1}^2$ +...+ $t_{i,o}^2$ + $It_i^2$)]<br>8:     if i = 1 then<br>9:       $d_{min}$ = d<br>10:      $U_{target}$ = 1     ▷ target represents a target patient portrait<br>11:     else if i ≠ 1 and d < $d_{min}$ then<br>12:       $d_{min}$ = d<br>13:       $U_{target}$ = i<br>14:     else<br>15:       pass<br>16:     end if<br>17:   end for<br>18: Output the corresponding caring program Mp of the patient portrait $U_{target}$ in the Kb |

In conclusion, the present disclosure first constructs the risk factor mining model of the cardiovascular and the drug attribute association mining model of the cardiovascular disease based on the consensus text data such as the data of the electronic medical record of the cardiovascular patient and the cardiovascular medication guideline to extract the clinical symptoms, the disease types, and the symptom diagnosis knowledge systems of the plurality of types of cardiovascular diseases. The clinical diagnostic dataset of the cardiovascular disease is constructed based on the clinical symptom of the cardiovascular disease, the disease type, and the symptom diagnosis knowledge system to train a type-based decision reasoning model of the cardiovascular disease, for example, the decision-supported TAN model. The medical convalescence knowledge base of the cardiovascular disease is constructed based on the convalescence data of the cardiovascular patient and the association rule mining model. A corresponding medical wellness program of the cardiovascular disease is recommended to a type-based patient based on the collaborative filtering algorithm and the medical convalescence knowledge base of the cardiovascular disease. Based on the above description, compared with the prior art, the present disclosure has following advantages:

(1) The present disclosure provides an intelligent decision reasoning method for type-based diagnosis and treatment of a cardiovascular disease, a device, and a product. Taking the decision-supported TAN model as an example, the present disclosure is used to achieve precise prediction of a fine-grained cardiovascular disease type and effectively promote precision medicine in the field.

(2) The present disclosure achieves efficient integration of the type-based decision support of the cardiovascular disease and the medical convalescence knowledge base of the cardiovascular disease. The confidence coefficient and the enhancement degree are assessed based on the association rule mining model to improve quality of the cardiovascular medical convalescence association rule set.

(3) The present disclosure implements a cardiovascular medical wellness program recommendation technology based on collaborative filtering, which can provide a target group with customized convalescence knowledge such as a drug, a diet, and exercise, effectively meeting a home-based wellness demand of the target group.

Embodiment 2

A computer device includes a memory, a processor, and a computer program stored in the memory and executable on the processor. The processor executes the computer program to perform the steps of the intelligent decision reasoning method for type-based diagnosis and treatment of a cardiovascular disease in Embodiment 1.

Embodiment 3

A computer-readable storage medium stores a computer program. The computer program is executed by a processor to perform the steps of the intelligent decision reasoning method for type-based diagnosis and treatment of a cardiovascular disease in Embodiment 1.

Embodiment 4

A computer program product includes a computer program. The computer program is executed by a processor to perform the steps of the intelligent decision reasoning method for type-based diagnosis and treatment of a cardiovascular disease in Embodiment 1.

Embodiment 5

A computer device is provided. The computer device may be a database. The computer device includes a processor, a memory, an input/output (I/O) interface, and a communication interface. The processor, the memory, and the I/O interface are connected through a system bus, and the communication interface is connected to the system bus through the I/O interface. The processor of the computer device is configured to provide computing and control capabilities. The memory of the computer device includes a nonvolatile storage medium and an internal memory. The nonvolatile storage medium stores an operating system, a computer program, and a database. The internal memory provides an environment for operation of the operating system and the computer program in the nonvolatile storage medium. The database of the computer device is configured to store a to-be-processed transaction. The I/O interface of the computer device is configured to exchange information between the processor and an external device. The communication interface of the computer device is configured to communicate with an external terminal through a network. The computer program is executed by the processor to implement the intelligent decision reasoning method for type-based diagnosis and treatment of a cardiovascular disease in Embodiment 1.

It should be noted that object information (including but not limited to object device information, object personal information, and the like) and data (including but not limited to data used for analysis, stored data, displayed data, and the like) involved in the present disclosure are all information and data authorized by an object or fully authorized by all parties, and collection, use, and processing of relevant data must comply with relevant laws, regulations, and standards of relevant countries and regions.

Those of ordinary skill in the art may understand that all or some of the procedures in the method of the foregoing embodiments may be implemented by a computer program instructing related hardware. The computer program may be stored in a nonvolatile computer-readable storage medium. When the computer program is executed, the procedures in the embodiments of the foregoing method may be performed. Any reference to a memory, a database, or other media used in the embodiments of the present disclosure may include at least one of a nonvolatile memory and a volatile memory. The nonvolatile memory may include a read-only memory (ROM), a magnetic tape, a floppy disk, a flash memory, an optical memory, a high-density embedded nonvolatile memory, a resistive random access memory (ReRAM), a magnetoresistive random access memory (MRAM), a ferroelectric random access memory (FRAM), a phase change memory (PCM), a graphene memory, and the like. The volatile memory may include a random access memory (RAM), an external cache memory, or the like. As an illustration rather than a limitation, the RAM may be in various forms, such as a static random access memory (SRAM), a dynamic random access memory (DRAM), or the like. The database involved in the embodiments provided in the present disclosure may include at least one of a relational database and a non-relational database. The non-relational database may include a blockchain-based distributed database or the like, but is not limited thereto. The processor involved in the embodiments provided in the present disclosure may be a general-purpose processor, a central processing unit, a graphics processor, a digital signal processor, a programmable logic unit, a data processing logic unit based on quantum computing, or the like, but is not limited thereto.

The technical characteristics of the above embodiments can be employed in arbitrary combinations. To provide a concise description of these embodiments, all possible combinations of all the technical characteristics of the above embodiments may not be described; however, these combinations of the technical characteristics should be construed as falling within the scope defined by the specification as long as no contradiction occurs.

Particular examples are used herein for illustration of the principles and implementation modes of the present disclosure. The descriptions of the above embodiments are merely used for assisting in understanding the method of the present disclosure and its core ideas, and references can be made to each other for the same and similar parts between embodiments. In addition, those of ordinary skill in the art can make various modifications in terms of particular implementations and the scope of application in accordance with the ideas of the present disclosure. In conclusion, the content of the specification shall not be construed as limitations to the present disclosure.

What is claimed is:

1. An intelligent decision reasoning method for type-based diagnosis and treatment of a cardiovascular disease, comprising:
    constructing a risk factor mining model of a cardiovascular disease and a drug attribute association mining model of the cardiovascular disease;
    extracting common clinical symptoms, disease types, and medication attribute information of a plurality of types of cardiovascular diseases from cardiovascular data based on the risk factor mining model of the cardiovascular disease and the drug attribute association mining model of the cardiovascular disease, wherein the cardiovascular data comprises: data of an electronic medical record of a cardiovascular patient, a cardiovascular medication guideline, clinical reception information, and expert consensus knowledge;
    constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases;
    constructing a type-based auxiliary diagnosis model of the cardiovascular disease based on the clinical diagnostic dataset and the clinical symptom diagnosis knowledge system of the cardiovascular disease, and using the type-based auxiliary diagnosis model of the cardiovascular disease for intelligent decision reasoning;
    constructing an association rule based on a reasoning result obtained through the intelligent decision reasoning;
    constructing a medical convalescence knowledge base of the cardiovascular disease based on convalescence data of the cardiovascular patient and the association rule;
    generating a recommended patient wellness program based on a collaborative filtering algorithm and the medical convalescence knowledge base of the cardiovascular disease; and
    treating the cardiovascular disease according to drug items of the recommended patient wellness program;
    wherein the constructing a risk factor mining model of a cardiovascular disease and a drug attribute association mining model of the cardiovascular disease comprises:
        extracting consensus text data by using a document parsing technology, wherein the consensus text data comprises text data of the electronic medical record of the cardiovascular patient and the cardiovascular medication guideline;
        adding a data annotation to the consensus text data to obtain annotated data, wherein the data annotation comprises an entity type, a relationship type, and an attribute type, the attribute type comprises a symptom, a cardiovascular disease type, a risk factor, a medical history, a biochemical indicator, a drug name, a medication type, a mode of administration, a medication frequency, a medication cycle, and a medication dosage;
        training a network model based on the annotated data, wherein the network model comprises an input layer, a text information representation and embedding layer, a semantic information modeling layer, a label sequence correction and recognition layer, and an output layer, wherein the input layer is configured to receive a training corpus for the risk factor mining model of the cardiovascular disease and the drug attribute association mining model of the cardiovascular disease, the text information representation and embedding layer comprises a Generalized Autoregressive Pretraining for Language Understanding (XLNet) network model integrating text semantic information and positional information to achieve corpus vectorization, the semantic information modeling layer comprises a Bi-directional Long Short-Term Memory (BiLSTM) network model comprising a forward Long Short-Term Memory (LSTM) layer capturing contextual information and a reverse LSTM layer capturing reverse information, the label sequence correction and recognition layer comprises a Conditional Random Field (CRF) network model configured to perform corrective recognition on a predicted label sequence output by the semantic information modeling layer, and obtain an optimal solution based on a probability relationship between adjacent labels, and the output layer is configured to generate a label sequence prediction result corresponding to a text corpus of the input layer; and
        separately using a trained network model as the risk factor mining model of the cardiovascular disease and the drug attribute association mining model of the cardiovascular disease.

2. The intelligent decision reasoning method for type-based diagnosis and treatment of a cardiovascular disease according to claim 1, wherein extracting the common clinical symptoms, the disease types, and the medication attribute information of the plurality of types of cardiovascular diseases from the consensus text data based on the risk factor mining model of the cardiovascular disease and the drug attribute association mining model of the cardiovascular disease specifically comprises:
    performing named entity recognition for the consensus text data based on the risk factor mining model of the cardiovascular disease, wherein recognized content comprises the symptom, the cardiovascular disease type, the risk factor, the medical history, and the biochemical indicator; and
    performing named entity recognition and association modeling of a cardiovascular related drug for the consensus text data based on the drug attribute association mining model of the cardiovascular disease to obtain recognized and mined content, wherein the recognized and mined content comprises the drug name, the medication type, the mode of administration, the medication frequency, the medication cycle, a dosage form, and the medication dosage.

3. The intelligent decision reasoning method for type-based diagnosis and treatment of a cardiovascular disease according to claim 1, wherein the constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases specifically comprises:

sorting out symptom data obtained by the risk factor mining model of the cardiovascular disease, and forming clinical diagnostic symptom indicators and expert clinical diagnosis knowledge systems of the plurality of types of cardiovascular diseases based on expert guidance, an expert experience knowledge system, and an expert consensus; and constructing the clinical diagnostic dataset of the cardiovascular disease based on the clinical diagnostic symptom indicators and types of the cardiovascular diseases; setting values of the clinical diagnostic symptom indicators of the cardiovascular diseases to 1, 0, or more clinically meaningful cardiovascular disease numbers or letters based on a symptom representation; and setting different values for different types of cardiovascular diseases to complete the construction of the clinical diagnostic dataset and the clinical symptom diagnosis knowledge system of the cardiovascular disease.

4. The intelligent decision reasoning method for type-based diagnosis and treatment of a cardiovascular disease according to claim 1, wherein a process of obtaining the reasoning result through the intelligent decision reasoning comprises:

determining conditional mutual information between symptom nodes, and ranking the conditional mutual information between the symptom nodes in descending order to obtain a set of the conditional mutual information between the symptom nodes;

based on the set of the conditional mutual information between the symptom nodes, designing a maximum weighted spanning tree according to a principle of selecting an edge without generating a loop;

adding a disease type node to the maximum weighted spanning tree to obtain a Bayesian network structure;

determining a conditional probability table of a Bayesian network based on the Bayesian network structure and the clinical diagnostic dataset of the cardiovascular disease;

forming a Tree-Augmented Naive Bayes (TAN) model for type-based decision-making of the cardiovascular disease based on the Bayesian network structure and the conditional probability table of the Bayesian network; and determining a probability of each cardiovascular disease type based on the type-based decision-supported TAN model of the cardiovascular disease, and selecting a type with a maximum probability as a disease type.

5. The intelligent decision reasoning method for type-based diagnosis and treatment of a cardiovascular disease according to claim 1, wherein the constructing a medical convalescence knowledge base of the cardiovascular disease based on convalescence data of the cardiovascular patient and the association rule specifically comprises:

constructing a medical convalescence transaction set of the cardiovascular disease based on the cardiovascular data, wherein the medical convalescence transaction set of the cardiovascular disease comprises medical convalescence transaction subsets of the plurality of types of cardiovascular diseases; a medical convalescence transaction subset of each type of cardiovascular disease comprises a corresponding patient portrait and a medical convalescence record set of the cardiovascular disease; the patient portrait comprises basic information and a disease type of a patient; the basic information of the patient comprises an age, a height, and a weight; the medical convalescence record set of the cardiovascular disease comprises a convalescence item; and the convalescence item comprises drug, diet, and exercise data;

when l=1, generating a frequent itemset 1 through screening based on a support degree of a single convalescence itemset, wherein the 1 represents a type of the medical convalescence transaction subset of the cardiovascular disease in the medical convalescence transaction set of the cardiovascular disease;

when l≥2, generating a candidate itemset 1 based on a frequent itemset (l−1);

searching for a non-frequent itemset (l−1) in the candidate itemset 1, and if the non-frequent itemset exists, performing pre-pruning to remove the non-frequent itemset;

generating a frequent itemset l through screening based on the candidate itemset 1 and the support degree, performing the step of generating the candidate itemset 1 based on the frequent itemset (l−1) when l≥2 until there is no itemset meeting a minimum support degree, and forming a set based on the frequent itemset l;

traversing an element in the set and determining a proper subset of the element, generating the association rule through permutation and combination, performing filtering based on a confidence coefficient and an enhancement degree to form a medical convalescence association rule set that is of the cardiovascular disease and corresponds to each type of patient portrait; and constructing the medical convalescence knowledge base of the cardiovascular disease based on the medical convalescence association rule set that is of the cardiovascular disease and corresponds to each type of patient portrait.

6. The intelligent decision reasoning method for type-based diagnosis and treatment of a cardiovascular disease according to claim 4, wherein the generating a recommended patient wellness program based on a collaborative filtering algorithm and the medical convalescence knowledge base of the cardiovascular disease specifically comprises:

marking basic information of a to-be-recommended patient, wherein the basic information comprises an age, a height, a weight, a medical history, a disease, and a treatment process;

inputting a clinical symptom of the to-be-recommended patient into the type-based decision-supported TAN model of the cardiovascular disease to output a cardiovascular disease typing result;

integrating the basic information of the to-be-recommended patient and the cardiovascular disease typing result to form a portrait of the to-be-recommended patient;

determining a distance between the portrait of the to-be-recommended patient and a patient portrait in the medical convalescence knowledge base of the cardiovascular disease; and selecting, from the medical convalescence knowledge base of the cardiovascular disease, a medical convalescence association rule set that is of the cardiovascular disease and corresponds to a patient portrait with a smallest distance from the portrait of the to-be-recommended patient as the recommended patient wellness program.

7. A computer device, comprising a memory, a processor, and a computer program stored in the memory and executable on the processor, wherein the processor executes the computer program to perform steps of an intelligent decision reasoning method for type-based diagnosis and treatment of a cardiovascular disease, and the intelligent decision reasoning method for type-based diagnosis and treatment of the cardiovascular disease comprises:

constructing a risk factor mining model of a cardiovascular disease and a drug attribute association mining model of the cardiovascular disease;

extracting common clinical symptoms, disease types, and medication attribute information of a plurality of types of cardiovascular diseases from cardiovascular data based on the risk factor mining model of the cardiovascular disease and the drug attribute association mining model of the cardiovascular disease, wherein the cardiovascular data comprises: data of an electronic medical record of a cardiovascular patient, a cardiovascular medication guideline, clinical reception information, and expert consensus knowledge;

constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases;

constructing a type-based auxiliary diagnosis model of the cardiovascular disease based on the clinical diagnostic dataset and the clinical symptom diagnosis knowledge system of the cardiovascular disease, and using the type-based auxiliary diagnosis model of the cardiovascular disease for intelligent decision reasoning;

constructing an association rule based on a reasoning result obtained through the intelligent decision reasoning;

constructing a medical convalescence knowledge base of the cardiovascular disease based on convalescence data of the cardiovascular patient and the association rule;

generating a recommended patient wellness program based on a collaborative filtering algorithm and the medical convalescence knowledge base of the cardiovascular disease; and treating the cardiovascular disease according to drug items of the recommended patient wellness program;

wherein the constructing a risk factor mining model of a cardiovascular disease and a drug attribute association mining model of the cardiovascular disease comprises:

extracting consensus text data by using a document parsing technology, wherein the consensus text data comprises text data of the electronic medical record of the cardiovascular patient and the cardiovascular medication guideline;

adding a data annotation to the consensus text data to obtain annotated data, wherein the data annotation comprises an entity type, a relationship type, and an attribute type; the attribute type comprises a symptom, a cardiovascular disease type, a risk factor, a medical history, a biochemical indicator, a drug name, a medication type, a mode of administration, a medication frequency, a medication cycle, and a medication dosage;

training a network model based on the annotated data, wherein the network model comprises an input layer, a text information representation and embedding layer, a semantic information modeling layer, a label sequence correction and recognition layer, and an output layer; wherein the input layer is configured to receive a training corpus for the risk factor mining model of the cardiovascular disease and the drug attribute association mining model of the cardiovascular disease; the text information representation and embedding layer comprises a Generalized Autoregressive Pretraining for Language Understanding (XLNet) network model integrating text semantic information and positional information to achieve corpus vectorization; the semantic information modeling layer comprises a Bi-directional Long Short-Term Memory (BiLSTM) network model comprising a forward Long Short-Term Memory (LSTM) layer capturing contextual information and a reverse LSTM layer capturing reverse information; the label sequence correction and recognition layer comprises a Conditional Random Field (CRF) network model configured to perform corrective recognition on a predicted label sequence output by the semantic information modeling layer, and obtain an optimal solution based on a probability relationship between adjacent labels; and the output layer is configured to generate a label sequence prediction result corresponding to a text corpus of the input layer; and separately using a trained network model as the risk factor mining model of the cardiovascular disease and the drug attribute association mining model of the cardiovascular disease.

8. The computer device according to claim 7, wherein extracting the common clinical symptoms, the disease types, and the medication attribute information of the plurality of types of cardiovascular diseases from the consensus text data based on the risk factor mining model of the cardiovascular disease and the drug attribute association mining model of the cardiovascular disease specifically comprises:

performing named entity recognition for the consensus text data based on the risk factor mining model of the cardiovascular disease, wherein recognized content comprises the symptom, the cardiovascular disease type, the risk factor, the medical history, and the biochemical indicator; and performing named entity recognition and association modeling of a cardiovascular related drug for the consensus text data based on the drug attribute association mining model of the cardiovascular disease to obtain recognized and mined content, wherein the recognized and mined content comprises the drug name, the medication type, the mode of administration, the medication frequency, the medication cycle, a dosage form, and the medication dosage.

9. The computer device according to claim 7, wherein the constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases specifically comprises:

sorting out symptom data obtained by the risk factor mining model of the cardiovascular disease, and forming clinical diagnostic symptom indicators and expert clinical diagnosis knowledge systems of the plurality of types of cardiovascular diseases based on expert guidance, an expert experience knowledge system, and an expert consensus; and constructing the clinical diagnostic dataset of the cardiovascular disease based on the clinical diagnostic symptom indicators and types of the cardiovascular diseases; setting values of the clinical diagnostic symptom indicators of the cardiovascular diseases to 1, 0, or more clinically meaningful cardiovascular disease numbers or letters based on a symptom representation; and setting different values for different types of cardiovascular diseases to complete the construction of the clinical diagnostic dataset and the clinical symptom diagnosis knowledge system of the cardiovascular disease.

10. The computer device according to claim 7, wherein a process of obtaining the reasoning result through the intelligent decision reasoning comprises:

determining conditional mutual information between symptom nodes, and ranking the conditional mutual information between the symptom nodes in descending order to obtain a set of the conditional mutual information between the symptom nodes;

based on the set of the conditional mutual information between the symptom nodes, designing a maximum weighted spanning tree according to a principle of selecting an edge without generating a loop;

adding a disease type node to the maximum weighted spanning tree to obtain a Bayesian network structure;

determining a conditional probability table of a Bayesian network based on the Bayesian network structure and the clinical diagnostic dataset of the cardiovascular disease;

forming a Tree-Augmented Naive Bayes (TAN) model for type-based decision-making of the cardiovascular disease based on the Bayesian network structure and the conditional probability table of the Bayesian network; and determining a probability of each cardiovascular disease type based on the type-based decision-supported TAN model of the cardiovascular disease, and selecting a type with a maximum probability as a disease type.

11. The computer device according to claim 7, wherein the constructing a medical convalescence knowledge base of the cardiovascular disease based on convalescence data of the cardiovascular patient and the association rule specifically comprises:

constructing a medical convalescence transaction set of the cardiovascular disease based on the cardiovascular data, wherein the medical convalescence transaction set of the cardiovascular disease comprises medical convalescence transaction subsets of the plurality of types of cardiovascular diseases; a medical convalescence transaction subset of each type of cardiovascular disease comprises a corresponding patient portrait and a medical convalescence record set of the cardiovascular disease; the patient portrait comprises basic information and a disease type of a patient; the basic information of the patient comprises an age, a height, and a weight; the medical convalescence record set of the cardiovascular disease comprises a convalescence item; and the convalescence item comprises drug, diet, and exercise data;

when l=1, generating a frequent itemset 1 through screening based on a support degree of a single convalescence itemset, wherein the 1 represents a type of the medical convalescence transaction subset of the cardiovascular disease in the medical convalescence transaction set of the cardiovascular disease;

when l≥2, generating a candidate itemset l based on a frequent itemset (l−1);

searching for a non-frequent itemset (l−1) in the candidate itemset l, and if the non-frequent itemset exists, performing pre-pruning to remove the non-frequent itemset;

generating a frequent itemset l through screening based on the candidate itemset l and the support degree, performing the step of generating the candidate itemset l based on the frequent itemset (l−1) when l≥2 until there is no itemset meeting a minimum support degree, and forming a set based on the frequent itemset l;

traversing an element in the set and determining a proper subset of the element, generating the association rule through permutation and combination, performing filtering based on a confidence coefficient and an enhancement degree to form a medical convalescence association rule set that is of the cardiovascular disease and corresponds to each type of patient portrait; and constructing the medical convalescence knowledge base of the cardiovascular disease based on the medical convalescence association rule set that is of the cardiovascular disease and corresponds to each type of patient portrait.

12. The computer device according to claim 10, wherein the generating a recommended patient wellness program based on a collaborative filtering algorithm and the medical convalescence knowledge base of the cardiovascular disease specifically comprises:

marking basic information of a to-be-recommended patient, wherein the basic information comprises an age, a height, a weight, a medical history, a disease, and a treatment process;

inputting a clinical symptom of the to-be-recommended patient into the type-based decision-supported TAN model of the cardiovascular disease to output a cardiovascular disease typing result;

integrating the basic information of the to-be-recommended patient and the cardiovascular disease typing result to form a portrait of the to-be-recommended patient:

determining a distance between the portrait of the to-be-recommended patient and a patient portrait in the medical convalescence knowledge base of the cardiovascular disease; and selecting, from the medical convalescence knowledge base of the cardiovascular disease, a medical convalescence association rule set that is of the cardiovascular disease and corresponds to a patient portrait with a smallest distance from the portrait of the to-be-recommended patient as the recommended patient wellness program.

13. A computer program product, comprising a computer program, wherein the computer program is executed by a processor to perform steps of an intelligent decision reasoning method for type-based diagnosis and treatment of a cardiovascular disease, and the intelligent decision reasoning method for type-based diagnosis and treatment of the cardiovascular disease comprises:

constructing a risk factor mining model of a cardiovascular disease and a drug attribute association mining model of the cardiovascular disease;

extracting common clinical symptoms, disease types, and medication attribute information of a plurality of types of cardiovascular diseases from cardiovascular data based on the risk factor mining model of the cardiovascular disease and the drug attribute association mining model of the cardiovascular disease, wherein the cardiovascular data comprises: data of an electronic medical record of a cardiovascular patient, a cardiovascular medication guideline, clinical reception information, and expert consensus knowledge;

constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases;

constructing a type-based auxiliary diagnosis model of the cardiovascular disease based on the clinical diagnostic dataset and the clinical symptom diagnosis knowledge system of the cardiovascular disease, and using the type-based auxiliary diagnosis model of the cardiovascular disease for intelligent decision reasoning;

constructing an association rule based on a reasoning result obtained through the intelligent decision reasoning;

constructing a medical convalescence knowledge base of the cardiovascular disease based on convalescence data of the cardiovascular patient and the association rule;

generating a recommended patient wellness program based on a collaborative filtering algorithm and the medical convalescence knowledge base of the cardiovascular disease; and treating the cardiovascular disease according to drug items of the recommended patient wellness program;

wherein the constructing a risk factor mining model of a cardiovascular disease and a drug attribute association mining model of the cardiovascular disease comprises:

extracting consensus text data by using a document parsing technology, wherein the consensus text data comprises text data of the electronic medical record of the cardiovascular patient and the cardiovascular medication guideline;

adding a data annotation to the consensus text data to obtain annotated data, wherein the data annotation comprises an entity type, a relationship type, and an attribute type; the attribute type comprises a symptom, a cardiovascular disease type, a risk factor, a medical history, a biochemical indicator, a drug name, a medication type, a mode of administration, a medication frequency, a medication cycle, and a medication dosage;

training a network model based on the annotated data, wherein the network model comprises an input layer, a text information representation and embedding layer, a semantic information modeling layer, a label sequence correction and recognition layer, and an output layer; wherein the input layer is configured to receive a training corpus for the risk factor mining model of the cardiovascular disease and the drug attribute association mining model of the cardiovascular disease; the text information representation and embedding layer comprises a Generalized Autoregressive Pretraining for Language Understanding (XLNet) network model integrating text semantic information and positional information to achieve corpus vectorization; the semantic information modeling layer comprises a Bi-directional Long Short-Term Memory (BiLSTM) network model comprising a forward Long Short-Term Memory (LSTM) layer capturing contextual information and a reverse LSTM layer capturing reverse information; the label sequence correction and recognition layer comprises a Conditional Random Field (CRF) network model configured to perform corrective recognition on a predicted label sequence output by the semantic information modeling layer, and obtain an optimal solution based on a probability relationship between adjacent labels; and the output layer is configured to generate a label sequence prediction result corresponding to a text corpus of the input layer; and separately using a trained network model as the risk factor mining model of the cardiovascular disease and the drug attribute association mining model of the cardiovascular disease.

14. The computer program product according to claim 13, wherein extracting the common clinical symptoms, the disease types, and the medication attribute information of the plurality of types of cardiovascular diseases from the consensus text data based on the risk factor mining model of the cardiovascular disease and the drug attribute association mining model of the cardiovascular disease specifically comprises:

performing named entity recognition for the consensus text data based on the risk factor mining model of the cardiovascular disease, wherein recognized content comprises the symptom, the cardiovascular disease type, the risk factor, the medical history, and the biochemical indicator; and performing named entity recognition and association modeling of a cardiovascular related drug for the consensus text data based on the drug attribute association mining model of the cardiovascular disease to obtain recognized and mined content, wherein the recognized and mined content comprises the drug name, the medication type, the mode of administration, the medication frequency, the medication cycle, a dosage form, and the medication dosage.

15. The computer program product according to claim 13, wherein the constructing a clinical diagnostic dataset and a clinical symptom diagnosis knowledge system of the cardiovascular disease through data preprocessing based on the common clinical symptoms, the disease types, and the medication attributes of the plurality of types of cardiovascular diseases specifically comprises:

sorting out symptom data obtained by the risk factor mining model of the cardiovascular disease, and forming clinical diagnostic symptom indicators and expert clinical diagnosis knowledge systems of the plurality of types of cardiovascular diseases based on expert guidance, an expert experience knowledge system, and an expert consensus; and constructing the clinical diagnostic dataset of the cardiovascular disease based on the clinical diagnostic symptom indicators and types of the cardiovascular diseases; setting values of the clinical diagnostic symptom indicators of the cardiovascular diseases to 1, 0, or more clinically meaningful cardiovascular disease numbers or letters based on a symptom representation; and setting different values for different types of cardiovascular diseases to complete the construction of the clinical diagnostic dataset and the clinical symptom diagnosis knowledge system of the cardiovascular disease.

16. The computer program product according to claim 13, wherein a process of obtaining the reasoning result through the intelligent decision reasoning comprises:
   determining conditional mutual information between symptom nodes, and ranking the conditional mutual information between the symptom nodes in descending order to obtain a set of the conditional mutual information between the symptom nodes;
   based on the set of the conditional mutual information between the symptom nodes, designing a maximum weighted spanning tree according to a principle of selecting an edge without generating a loop;
   adding a disease type node to the maximum weighted spanning tree to obtain a Bayesian network structure;
   determining a conditional probability table of a Bayesian network based on the Bayesian network structure and the clinical diagnostic dataset of the cardiovascular disease;
   forming a Tree-Augmented Naive Bayes (TAN) model for type-based decision-making of the cardiovascular disease based on the Bayesian network structure and the conditional probability table of the Bayesian network; and
   determining a probability of each cardiovascular disease type based on the type-based decision-supported TAN model of the cardiovascular disease, and selecting a type with a maximum probability as a disease type.

17. The computer program product according to claim 13, wherein the constructing a medical convalescence knowledge base of the cardiovascular disease based on convalescence data of the cardiovascular patient and the association rule specifically comprises:
   constructing a medical convalescence transaction set of the cardiovascular disease based on the cardiovascular data, wherein the medical convalescence transaction set of the cardiovascular disease comprises medical convalescence transaction subsets of the plurality of types of cardiovascular diseases; a medical convalescence transaction subset of each type of cardiovascular disease comprises a corresponding patient portrait and a medical convalescence record set of the cardiovascular disease; the patient portrait comprises basic information and a disease type of a patient; the basic information of the patient comprises an age, a height, and a weight; the medical convalescence record set of the cardiovascular disease comprises a convalescence item; and the convalescence item comprises drug, diet, and exercise data;
   when l=1, generating a frequent itemset 1 through screening based on a support degree of a single convalescence itemset, wherein the 1 represents a type of the medical convalescence transaction subset of the cardiovascular disease in the medical convalescence transaction set of the cardiovascular disease;
   when l≥2, generating a candidate itemset 1 based on a frequent itemset (l−1);
   searching for a non-frequent itemset (l−1) in the candidate itemset 1, and if the non-frequent itemset exists, performing pre-pruning to remove the non-frequent itemset;
   generating a frequent itemset l through screening based on the candidate itemset 1 and the support degree, performing the step of generating the candidate itemset 1 based on the frequent itemset (l−1) when l≥2 until there is no itemset meeting a minimum support degree, and forming a set based on the frequent itemset l;
   traversing an element in the set and determining a proper subset of the element, generating the association rule through permutation and combination, performing filtering based on a confidence coefficient and an enhancement degree to form a medical convalescence association rule set that is of the cardiovascular disease and corresponds to each type of patient portrait; and
   constructing the medical convalescence knowledge base of the cardiovascular disease based on the medical convalescence association rule set that is of the cardiovascular disease and corresponds to each type of patient portrait.

* * * * *